US011774452B2

(12) United States Patent
Alper

(10) Patent No.: US 11,774,452 B2
(45) Date of Patent: Oct. 3, 2023

(54) ANTIBODIES AGAINST CARCINOEMBRYONIC ANTIGENS

(71) Applicant: American Diagnostics & Therapy, LLC, Rockville, MD (US)

(72) Inventor: Özge Alper, Rockville, MD (US)

(73) Assignee: American Diagnostics & Therapy, LLC, Rockville, MD (US)

( * ) Notice: Subject to any disclaimer, the term of this patent is extended or adjusted under 35 U.S.C. 154(b) by 0 days.

(21) Appl. No.: 18/164,206

(22) Filed: Feb. 3, 2023

(65) Prior Publication Data

US 2023/0194533 A1 Jun. 22, 2023

Related U.S. Application Data

(63) Continuation of application No. PCT/US2022/079296, filed on Nov. 4, 2022.

(60) Provisional application No. 63/336,676, filed on Apr. 29, 2022, provisional application No. 63/275,998, filed on Nov. 5, 2021.

(51) Int. Cl.
*C07K 16/30* (2006.01)
*G01N 33/574* (2006.01)

(52) U.S. Cl.
CPC ... *G01N 33/57473* (2013.01); *C07K 16/3007* (2013.01); *C07K 2317/565* (2013.01)

(58) Field of Classification Search
CPC .......... G01N 33/57473; C07K 16/3007; C07K 2317/565
See application file for complete search history.

(56) References Cited

U.S. PATENT DOCUMENTS

| | | | |
|---|---|---|---|
| 4,816,567 A | 3/1989 | Cabilly et al. |
| 5,208,020 A | 5/1993 | Chari et al. |
| 5,500,362 A | 3/1996 | Robinson et al. |
| 5,624,821 A | 4/1997 | Winter et al. |
| 5,648,237 A | 7/1997 | Carter |
| 5,789,199 A | 8/1998 | Joly et al. |
| 5,821,337 A | 10/1998 | Carter et al. |
| 5,840,523 A | 11/1998 | Simmons et al. |
| 5,959,177 A | 9/1999 | Hein et al. |
| 6,040,498 A | 3/2000 | Stomp et al. |
| 6,171,586 B1 | 1/2001 | Lam et al. |
| 6,194,551 B1 | 2/2001 | Idusogie et al. |
| 6,267,958 B1 | 7/2001 | Andya et al. |
| 6,417,429 B1 | 7/2002 | Hein et al. |
| 6,420,548 B1 | 7/2002 | Vézina et al. |
| 6,602,684 B1 | 8/2003 | Umaña et al. |
| 6,737,056 B1 | 5/2004 | Presta |
| 7,125,978 B1 | 10/2006 | Vézina et al. |
| 7,332,581 B2 | 2/2008 | Presta |
| 7,371,826 B2 | 5/2008 | Presta |
| 7,521,541 B2 | 4/2009 | Eigenbrot et al. |
| 2002/0164328 A1 | 11/2002 | Shinkawa et al. |
| 2003/0115614 A1 | 6/2003 | Kanda et al. |
| 2003/0157108 A1 | 8/2003 | Presta |
| 2004/0093621 A1 | 5/2004 | Shitara et al. |
| 2004/0109865 A1 | 6/2004 | Niwa et al. |
| 2004/0110282 A1 | 6/2004 | Kanda et al. |
| 2004/0110704 A1 | 6/2004 | Yamane et al. |
| 2004/0132140 A1 | 7/2004 | Satoh et al. |
| 2005/0014934 A1 | 1/2005 | Hinton et al. |
| 2005/0123546 A1 | 6/2005 | Umana et al. |
| 2005/0216958 A1 | 9/2005 | Yamane et al. |
| 2005/0260186 A1 | 11/2005 | Bookbinder et al. |
| 2006/0104968 A1 | 5/2006 | Bookbinder et al. |
| 2015/0147333 A1 | 5/2015 | Storm et al. |

FOREIGN PATENT DOCUMENTS

| | | |
|---|---|---|
| WO | 9429351 A2 | 12/1994 |
| WO | 1997030087 A1 | 8/1997 |
| WO | 1998058964 A1 | 12/1998 |
| WO | 1999022764 A1 | 5/1999 |
| WO | 9951642 A1 | 10/1999 |
| WO | 0061739 A1 | 10/2000 |
| WO | 0129246 A1 | 4/2001 |
| WO | 0231140 A1 | 4/2002 |
| WO | 2003011878 A2 | 2/2003 |
| WO | 03085119 A1 | 10/2003 |
| WO | 2005035586 A1 | 4/2005 |
| WO | 2005035778 A1 | 4/2005 |
| WO | 2004056312 A3 | 5/2005 |
| WO | 2005053742 A1 | 6/2005 |
| WO | 2005100402 A1 | 10/2005 |
| WO | 2006029879 A2 | 3/2006 |
| WO | 2006044908 A2 | 4/2006 |
| WO | 2008077546 A1 | 7/2008 |
| WO | 2020113164 A1 | 6/2020 |
| WO | 2020160560 A2 | 8/2020 |

OTHER PUBLICATIONS

Paul, WE (1993) Fundamental Immunology, 3rd ed. Raven Press, NY, Chap. 9, pp. 292-295.*
Rudikoff, S et al. (1982) Proc. Natl. Acad. Sci. USA, 79:1979-1983 (doi: 10.1073/pnas.79.6.1979).*
Colman, PM (1994) Research in Immunology, Elsevier, NY, 145(1):33-36.*
Bendig M. M. (1995) Methods: A Companion to Methods in Enzymology, 8:83-93.*
MacCallum et al. (Oct. 11, 1996) J. Mol. Biol., 262(5):732-745. (doi: 10.1006/jmbi.1996.0548).*
Casset et al (2003) Biochemical and Biophysical Research Communications, 307:198-205. (doi:10.1016/S0006-291X(03)01131-8).*

(Continued)

*Primary Examiner* — Robert S Landsman
(74) *Attorney, Agent, or Firm* — McNeill Baur PLLC

(57) ABSTRACT

The invention provides an anti-CEA antibody for use in detecting CEA, treating disorders associated with CEA expression, diagnosing cancers characterized by aberrant CEA expression, and predicting effectiveness of cancer drug therapies.

5 Claims, 14 Drawing Sheets

Specification includes a Sequence Listing.

(56) References Cited

OTHER PUBLICATIONS

Chen et al. (1995) EMBO J., 14(12):2784-2794. (doi: 10.1002/j.1460-2075.1995.tb07278.x).*
PCT International Search Report and Written Opinion from PCT/US22/79296, dated Mar. 6, 2023, 11 pages.
Beauchemin, Nicole et al., "Carcinoembryonic antigen-related cell adhesion molecules (CEACAMs) in cancer progression and metastatis", Cancer Metastasis Rev. 2013; 32(3-4): 643-71.
Blumenthal, Rosalyn D. et al., "Expression patterns of CEACAM5 and CEACAM6 in primary and metastatic cancers", BMC Cancer 2007, 7:2, 1-15.
Bruggemann, Marianne et al., "Comparison of the Effector Functions of Human Immunoglobulins Using a Matched Set of Chimeric Antibodies", J Exp Med, vol. 166, 1351-1361, Nov. 1987.
Chari, Ravi V.J. et al., "Immunoconjugates Containing Novel Maytansinoids: Promising Anticancer Drugs", Cancer Research 52, 127-131, 1992.
Charlton, Keith A., "Expression and Isolation of Recombinant Antibody Fragments in E. coli", Methods in Molecular Biology, vol. 248, 2003, 245-254.
Clackson, Tim et al., "Making antibody fragments using phage display libraries", Nature 352, 624-628 (1991).
Clynes, Raphael et al., "Fc receptors are required in passive and active immunity to melanoma", PNAS, vol. 95, 652-656, Jan. 1998.
Cragg, Mark S. et al., "Antibody specificity controls in vivo effector mechanisms of anti-CD20 reagents", Blood, 2004, 103: 2738-2743.
Cragg, Mark S. et al., "Complement-mediated lysis by anti-CD20 mAb correlates with segregation into lipid rafts", Immunobiology, Blood, 2003, vol. 101, No. 3, 1045-1052.
Dattamajumdar, Anupam K. et al., "Rapid cloning of any rearranged mouse immunoglobulin variable genes", Immunogenetics 43, 141-151 (1996).
Duncan, Alexander R. et al., "The binding site for C1q on IgG", Nature, 1988, vol. 332, 738-740.
Flatman, Stephen et al., "Process analytics for purification of monoclonal antibodies", Journal of Chromatography B, 848 (2007) 79-87.
Gazzano-Santoro, Helene et al., "A non-radioactive complement-dependent cytotoxicity assay for anti-CD20 monoclonal antibody", Journal of Immunological Methods 202 (1997) 163-171.
Gerngross, Tillman U., "Advances in the production of human therapeutic proteins in yeasts and filamentous fungi", Nature Biotechnology, vol. 22, No. 11, Nov. 2004, 1409-1414.
Gold, Phil et al., "Specific Carcinoembryonic Antigens of the Human Digestive System", J Exp Med, 1965, 122(3):467-81.
Graham, F.L. et a., "Characteristics of a Human Cell Line Transformed by DNA from Human Adenovirus Type 5", J. gen. Virol. (1977) 36, 59-72.
Guyer, Ruth L. et al., "Immunoglobulin Binding by Mouse Intestinal Epithelial Cell Receptors", J. Immunology, vol. 117, No. 2, 1976, 587-593.
Hellstrom, Ingegerd et al., "Antitumor effects of L6, an IgG2a antibody that reacts with most human carcinomas", PNAS, vol. 83, 7059-7063, Sep. 1986.
Hellstrom, Ingegerd et al., "Strong antitumor activities of IgG3 antibodies to a human melanoma-associated ganglioside", PNAS, vol. 82, 1499-1502, Mar. 1985.
Idusogie, Esohe E. et al., "Mapping of the C1q Binding Site on Rituxan, a Chimeric Antibody with a Human IgG1 Fc", J Immunol 2000; 164:4178-4184.
Kam, Nadine Wong Shi et al., "Carbon nanotubes as multifunctional biological transporters and near-infrared agents for selective cancer cell destruction", PNAS, vol. 102, No. 33, 11600-11605, Aug. 16, 2005.

Kanda, Yutaka et al., "Comparison of Cell Lines for Stable Production of Fucose-Negative Antibodies With Enhanced ADCC", Biotechnology and Bioengineering, 94(4) 2006, 680-688.
Kim, Jin-Kyoo et al., "Localization of the site of the murine IgG1 molecular that is involved in binding to the murine Intestinal Fc receptor", Eur. J. Immunol. 1994, 24: 2429-2434.
Kindt et al., Kuby Immunology, 6th edition, p. 91, 2007.
Li, Huijuan et al., "Optimization of humanized IgGs in glycoengineered Pichia pastoris", Nature Biotechnology, vol. 24, No. 2, Feb. 2006, 210-215.
Locker, Gershon Y. et al., "ASCO 2006 Update of Recommendation for the Use of Tumor Markers in Gastrointestinal Cancer", Journal of Clinical Oncology, 2006, vol. 24, No. 33, 5313-5327.
Mather, Jennie P. et al., "Culture of Testicular Cells in Hormone-Supplemented Serum-Free Medium", Annals N.Y. Aad. Sci. 383:44-68 (1982).
Mather, Jennie P., "Establishment and Characterization of Two Distinct Mouse Testicular Epithelial Cell Lines", Biology of Reproduction 23, 243-252 (1980).
Moretto, Roberto et al., "CEA increase as a marker of disease progression after first-line induction therapy in metastatic colorectal cancer patients. A pooled analysis of TRIBE and TRIBE2 studies", British Journal of Cancer, 2021, 125(6) 839-845.
Okazaki, Akira et al., "Fucose Depletion from human IgG1 Oligosaccharide Enhances Binding Enthalpy and Association Rate Between IgG1 and FcγRIIIa", J. Mol. Biol (2004) 336, 1239-1249.
Petkova, Stefka B. et al., "Enhanced half-life of genetically engineered human IgG1 antibodies in a humanized FcRn mouse model: potential application in humorally mediated autoimmune disease", International Immunology, vol. 18, No. 12, 1759-1769, 2006.
Portolano, Stefano et al., "Lack of Promiscuity in Autoantigen-Specific H and L Chain Combinations as Revealed by Human H and L Chain Roulette", The Journal of Immunology, vol. 150, 88-0887, No. 3, 1993.
Ravetch, Jeffrey V. et al., "Fc Receptors", Annu. Rev. Immunol. 1991, 9:457-92.
Ripka, James et al., "Two Chinese Hamster Ovary Glycosylation Mutants Affected in the Conversion of GDP-Mannose to GDP-Fucose", Archives of Biochemistry and Biophysics, vol. 249, No. 2, 1986, 533-545.
Shields, Robert L. et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, vol. 276, No. 9, 6591-6604, 2001.
Urlaub, Gail et al., "Isolation of Chinese hamster cell mutants deficient in dihydrofolate reductase activity", PNAS, vol. 77, No. 7, 4216-4220, Jul. 1980.
Vitetta, Ellen S. et al., "Redesigning Nature's Poisons to Create Anti-Tumor Reagents", Science, vol. 238: 1098-1104, 1987.
Wright, Ann et al., "Effect of glycosylation on antibody function: implications for genetic engineering", TIBTECH, Jan. 1997, vol. 15, 26-32.
Yamane-Ohnuki, Naoko et al., "Establishment of FUT8 knockout Chinese hamster ovary cells: an ideal host cell line for producting completely defucosylated antibodies with enhanced antibody-dependent cellular cytotoxicity", Biotechnol Bioeng. Sep. 5, 2004, 87(5): 614-622.
Yazaki, Paul J. et al., "Expression of Recombinant Antibodies in Mammalian Cell Lines", Methods in Molecular Biology, vol. 248, 255-268 (2003).
Yu, Ping et al., "The dynamic monitoring of CEA in response to chemotherapy and prognosis of mCRC patients", BMC Cancer (2018) 18:1076.

* cited by examiner

Fig. 2

```
                              <----------------------------FR1-IMGT------------------------------><-----CDR1-IM
                               D  I  L  M  T  Q  S  P  S  S  L  S  A  S  L  G  G  T  V  T  I  T  C  K  A  S  Q  D  I  N
V              Query_1       1 GACATTCTGATGACCCAGTCTCCATCCTCTCTGTCTGCATCTCTGGGAGGCACAGTCACCATCACTTGCAAGGCCAGCCAGGACATAAAC    90
V  80.9% (225/278) IGKV1-33*01  1 ...C.A...........................................G.A......A.G...........C......T.G........    90
V  80.9% (225/278) IGKV1D-33*01 1 ...C.A...........................................G.A......A.G...........C......T.G........    90
V  79.1% (216/273) IGKV1-27*01  1 D  I  Q  M  T  Q  S  P  S  S  L  S  A  S  V  G  D  R  V  T  I  T  C  Q  A  S  Q  D  I  S
                                ...C.A...........................................G.A......A.G..........CG......T.G........    90

GT-><-----------FR2-IMGT---------------><CDR2-IM><------------------FR3-IMGT
                               K  Y  I  A  W  Y  Q  H  K  P  G  K  G  P  R  L  L  I  H  Y  T  S  T  L  Q  P  A  I  P  S
V              Query_1      91 AAGTATATAGCTTGGTACCAACACAAGCCTGGAAAAGGTCCTAGGCTGCTCATACATTACACATCTACATTACAGCCAGCCATCCATCA   180
V  80.9% (225/278) IGKV1-33*01 91 ...C...T..AA......T.G.G.A.A.G....CC......A..C.G..CT.CG.TG.....C.AT..GG.AA...GGG........   180
V  80.9% (225/278) IGKV1D-33*01 91 ...C...T..AA......T.G.G.A.A.G....CC......A..C.G..CT.CG.TG.....C.AT..GG.AA...GGG........   180
V  79.1% (216/273) IGKV1-27*01 91   N  Y  L  N  W  Y  Q  Q  K  P  G  K  A  P  K  L  L  I  Y  D  A  S  N  L  E  T  G  V  P  S
                                ...T...T....C......T.G.G.A.A.G....T.........A.C.G..CT..GCTG.....C..T..G.AT..GGG........T  180

<--------------------FR3-IMGT-------------------------------><----><----
                               R  F  S  G  S  G  S  G  R  D  Y  S  F  S  I  S  N  L  E  P  E  D  I  A  T  Y  Y  C  L  Q
V              Query_1     181 AGGTTCAGTGGCAGTGGATCTGGGACAGATTATTCCTTCAGCATCAGCAACCTGGAGCCTGAAGATATTGCAACTTATTATTGTCTACAG   270
V  80.9% (225/278) IGKV1-33*01 181 ........................A...C..T.A.T..C.......C.........G...........A.....C...A.....   270
V  80.9% (225/278) IGKV1D-33*01 181 ........................A...C..T.A.T..C.......C.........G...........A.....C...A.....   270
V  79.1% (216/273) IGKV1-27*01 181   R  F  S  G  S  G  S  G  T  D  F  T  F  T  I  S  S  L  Q  P  E  D  I  A  T  Y  Y  C  Q  Q
                               C...........................TCA.TC...C.........G.............C.............A.A.....   270

CDR3-IMGT-->
                               Y  D  N  T  F  D  A  G  T  K  L  E  I  K
V              Query_1     271 TATGATAACACGTTCGATGCTGGGACCAAGCTGGAAATAAAA                                    312 (SEQ ID NO:23)
V  80.9% (225/278) IGKV1-33*01 271 .........                                                                      278 (SEQ ID NO:24)
V  80.9% (225/278) IGKV1D-33*01 271   Y  D                                                                         278 (SEQ ID NO:25)
V  79.1% (216/273) IGKV1-27*01 271 .........                                                                          (SEQ ID NO:26)
                                C.........                                                                    278 (SEQ ID NO:27)
                                                                                                              273 (SEQ ID NO:28)
J  90.5% (19/21) IGKJ1*01   17 ..............G........C...                                                   37
J  90.5% (19/21) IGKJ2*01   18 ......................G.C...                                                 38
J  90.5% (19/21) IGKJ2*02   17 ......................G.C...                                                 37
```

*Fig. 3*

SEQUENCE LISTING

```
Sequence total quantity: 28
SEQ ID NO: 1            moltype = AA  length = 8
FEATURE                 Location/Qualifiers
REGION                  1..8
                        note = HCDR1
source                  1..8
                        mol_type = protein
                        organism = synthetic construct
SEQUENCE: 1
GFSLTSNG                                                            8

SEQ ID NO: 2            moltype = AA  length = 7
FEATURE                 Location/Qualifiers
REGION                  1..7
                        note = HCDR2
source                  1..7
                        mol_type = protein
                        organism = synthetic construct
SEQUENCE: 2
IWAGGNT                                                             7

SEQ ID NO: 3            moltype = AA  length = 12
FEATURE                 Location/Qualifiers
REGION                  1..12
                        note = HCDR3
source                  1..12
                        mol_type = protein
                        organism = synthetic construct
SEQUENCE: 3
ARDDGYYYAM DY                                                      12

SEQ ID NO: 4            moltype = AA  length = 6
FEATURE                 Location/Qualifiers
REGION                  1..6
                        note = LCDR1
source                  1..6
                        mol_type = protein
                        organism = synthetic construct
SEQUENCE: 4
QDINKY                                                              6

SEQ ID NO: 5            moltype =     length =
SEQUENCE: 5
000
```

```
SEQ ID NO: 6              moltype = AA  length = 6
FEATURE                   Location/Qualifiers
REGION                    1..6
                          note = LCDR3
source                    1..6
                          mol_type = protein
                          organism = synthetic construct
SEQUENCE: 6
LQYDNT                                                                    6

SEQ ID NO: 7              moltype = AA  length = 97
FEATURE                   Location/Qualifiers
REGION                    1..97
                          note = VH
source                    1..97
                          mol_type = protein
                          organism = synthetic construct
SEQUENCE: 7
EVQLEESGPG LVAPSQSLSI TCTVSGFSLT SNGVHWVRQP PGKGLEWLGI IWAGGNTNYN         60
SALMSRLSIG KDNSKSQVFL KMNSLQTDDT AMYYCAR                                  97

SEQ ID NO: 8              moltype = AA  length = 92
FEATURE                   Location/Qualifiers
REGION                    1..92
                          note = VL
source                    1..92
                          mol_type = protein
                          organism = synthetic construct
SEQUENCE: 8
DILMTQSPSS LSASLGGTVT ITCKASQDIN KYIAWYQHKP GKGPRLLIHY TSTLQPAIPS         60
RFSGSGSGRD YSFSISNLEP EDIATYYCLQ YD                                       92

SEQ ID NO: 9              moltype = AA  length = 116
FEATURE                   Location/Qualifiers
REGION                    1..116
                          note = Full Heavy V-D-J-REGION
source                    1..116
                          mol_type = protein
                          organism = synthetic construct
SEQUENCE: 9
EVQLEESGPG LVAPSQSLSI TCTVSGFSLT SNGVHWVRQP PGKGLEWLGI IWAGGNTNYN         60
SALMSRLSIG KDNSKSQVFL KMNSLQTDDT AMYYCARDDG YYYAMDYWGQ GTTVTR            116

SEQ ID NO: 10             moltype = AA  length = 104
FEATURE                   Location/Qualifiers
REGION                    1..104
                          note = Full Light V-J-REGION
source                    1..104
                          mol_type = protein
                          organism = synthetic construct
SEQUENCE: 10
DILMTQSPSS LSASLGGTVT ITCKASQDIN KYIAWYQHKP GKGPRLLIHY TSTLQPAIPS         60
RFSGSGSGRD YSFSISNLEP EDIATYYCLQ YDNTFDAGTK LEIK                         104

SEQ ID NO: 11             moltype = AA  length = 345
FEATURE                   Location/Qualifiers
REGION                    1..345
                          note = Nucleotide Sequence Heavy Chain
source                    1..345
                          mol_type = protein
                          organism = synthetic construct
SEQUENCE: 11
TGAGGTGCAG CTGGAGGAGT CAGGACCTGG CCTGGTGGCG CCCTCACAGA GCCTGTCCAT         60
CACTTGCACT GTCTCTGGGT TTTCATTAAC CAGCAATGGT GTACACTGGG TTCGCCAGCC        120
TCCAGGAAAG GGTCTGGAGT GGCTGGGAAT AATATGGGCT GGTGGAAACA CAAATTATAA        180
TTCGGCTCTC ATGTCCAGAC TGAGCATCGG CAAAGACAAC TCCAAGAGTC AAGTTTTCTT        240
AAAAATGAAC AGTCTGCAAA CTGATGACAC AGCCATGTAC TACTGTGCCA GAGATGATGG        300
TTACTACTAT GCTATGGACT ACTGGGGCCA AGGGACCACG GTCAC                       345

SEQ ID NO: 12             moltype = AA  length = 311
FEATURE                   Location/Qualifiers
REGION                    1..311
                          note = Nucleotide Sequence Light Chain
source                    1..311
                          mol_type = protein
                          organism = synthetic construct
SEQUENCE: 12
GACATTCTGA TGACCCAGTC TCCATCCTCA CTGTCTGCAT CTCTGGGAGG CACAGTCACC         60
```

```
                             -continued
ATCACTTGCA AGGCGAGCCA GGACATAAAC AAGTATATAG CTTGGTACCA ACACAAGCCT   120
GGAAAAGGTC CTAGGCTGCT CATACATTAC ACATCTACAT TACAGCCAGC CATCCCATCA   180
AGGTTCAGTG GAAGTGGGTC TGGGAGAGAT TATTCCTTCA GCATCAGCAA CCTGGAGCCT   240
GAAGATATTG CAACTTATTA TTGTCTACAG TATGATAACA CGTTCGATGC TGGGACCAAG   300
CTGGAAATAA A                                                       311

SEQ ID NO: 13           moltype = AA   length = 21
FEATURE                 Location/Qualifiers
REGION                  1..21
                        note = VH Primer Sequence
source                  1..21
                        mol_type = protein
                        organism = synthetic construct
SEQUENCE: 13
TGAGGTGCAG CTGGAGGAGT C                                            21

SEQ ID NO: 14           moltype = AA   length = 24
FEATURE                 Location/Qualifiers
REGION                  1..24
                        note = JH Primer Sequence
source                  1..24
                        mol_type = protein
                        organism = synthetic construct
SEQUENCE: 14
GTGACCGTGG TCCCTTGGCC CCAG                                         24

SEQ ID NO: 15           moltype = AA   length = 21
FEATURE                 Location/Qualifiers
REGION                  1..21
                        note = VK Primer Sequence
source                  1..21
                        mol_type = protein
                        organism = synthetic construct
SEQUENCE: 15
GACATTCTGA TGACCCAGTC T                                            21

SEQ ID NO: 16           moltype = AA   length = 21
FEATURE                 Location/Qualifiers
REGION                  1..21
                        note = JK Prime Sequence
source                  1..21
                        mol_type = protein
                        organism = synthetic construct
SEQUENCE: 16
TTTTATTTCC AGCTTGGTCC C                                            21

SEQ ID NO: 17           moltype = AA   length = 114
FEATURE                 Location/Qualifiers
REGION                  1..114
                        note = ADx-CEA heavy chain
source                  1..114
                        mol_type = protein
                        organism = synthetic construct
SEQUENCE: 17
VQLEESGPGL VAPSQSLSIT CTVSGFSLTS NGVHWVRQPP GKGLEWLGII WAGGNTNYNS   60
ALMSRLSIGK DNSKSQVFLK MNSLQTDDTA MYYCARDDGY YYAMDYWGQG TTVT         114

SEQ ID NO: 18           moltype = DNA   length = 343
FEATURE                 Location/Qualifiers
misc_feature            1..343
                        note = ADx-CEA heavy chain
source                  1..343
                        mol_type = other DNA
                        organism = synthetic construct
SEQUENCE: 18
aggtgcagct ggaggagtca ggacctggcc tggtggcgcc ctcacagagc ctgtccatca   60
cttgcactgt ctctgggttt tcattaacca gcaatggtgt acactgggtt cgccagcctc   120
caggaaaggg tctggagtgg ctgggaataa tatgggctgg tggaaacaca aattataatt   180
cggctctcat gtccagactg agcatcggca aagacaactc caagagtcaa gtttccttaa   240
aaatgaacag tctgcaaact gatgacacag ccatgtacta ctgtgccaga gatgatggtt   300
actactatgc tatggactac tggggccaag ggaccacggt cac                    343

SEQ ID NO: 19           moltype = DNA   length = 96
FEATURE                 Location/Qualifiers
misc_feature            1..96
                        note = IGHV4-4*02
source                  1..96
                        mol_type = other DNA
                        organism = synthetic construct
```

```
SEQUENCE: 19
cgcaaaatgg gcccgtggcc acgtgaactg gtccggatgg acatcaaggc cccctcaagt    60
cgccatcagt gacgtccggg cgtcgaccgc cgggtg                              96

SEQ ID NO: 20            moltype = AA   length = 97
FEATURE                  Location/Qualifiers
REGION                   1..97
                         note = IGHV4-4*02
source                   1..97
                         mol_type = protein
                         organism = synthetic construct
SEQUENCE: 20
VQLQESGPGL VKPSGTLSLT CAVSGGSISS SNWWSWVRQP PGKGLEWIGE IYHSGSTAAD    60
TAVYYCARNY NPSLKSRVTI SVDKSKNQFS LKLSSVT                             97

SEQ ID NO: 21            moltype = DNA   length = 99
FEATURE                  Location/Qualifiers
misc_feature             1..99
                         note = IGHV3-33*08
source                   1..99
                         mol_type = other DNA
                         organism = synthetic construct
SEQUENCE: 21
ttggggagcca tgggagtcag actctgacac accgttcagc gcggcgttaa gtatactgaa   60
ctcggaggct cctcgtacac gcgatcgcca ggcggtgtg                           99

SEQ ID NO: 22            moltype = DNA   length = 101
FEATURE                  Location/Qualifiers
misc_feature             1..101
                         note = IGHV4-30-4*01
source                   1..101
                         mol_type = other DNA
                         organism = synthetic construct
SEQUENCE: 22
cgcaaaatcc ctggccacgt ggatacttgg agtaccgcat gtaccattac aggctcccct    60
caagtcgtca tcagtcgacg tcccggcgtc gactgccagg t                       101

SEQ ID NO: 23            moltype = AA   length = 104
FEATURE                  Location/Qualifiers
REGION                   1..104
                         note = ADx-CEA light chain
source                   1..104
                         mol_type = protein
                         organism = synthetic construct
SEQUENCE: 23
DILMTQSPSS LSASLGGTVT ITCKASQDIN KYIAWYQHKP GKGPRLLIHY TSTLQPAIPS    60
RFSGSGSGRD YSFSISNLEP EDIATYYCLQ YDNTFDAGTK LEIK                    104

SEQ ID NO: 24            moltype = DNA   length = 312
FEATURE                  Location/Qualifiers
misc_feature             1..312
                         note = ADx-CEA light chain
source                   1..312
                         mol_type = other DNA
                         organism = synthetic construct
SEQUENCE: 24
gacattctga tgacccagtc tccatcctca ctgtctgcat ctctgggagg cacagtcacc    60
atcacttgca aggcgagcca ggacataaac aagtatatag cttggtacca acacaagcct  120
ggaaaaggtc ctaggctgct catacattac acatctacat tacagccagc catcccatca  180
aggttcagtg gaagtgggtc tgggagagat tattccttca gcatcagcaa cctggagcct  240
gaagatattg caacttatta ttgtctacag tatgataaca cgttcgatgc tgggaccaag  300
ctggaaataa aa                                                      312

SEQ ID NO: 25            moltype = DNA   length = 53
FEATURE                  Location/Qualifiers
misc_feature             1..53
                         note = IGKV1-33*01
source                   1..53
                         mol_type = other DNA
                         organism = synthetic construct
SEQUENCE: 25
cacgaagctt gctaatggaa gccacgctcg tgcatggaag ggactatcgc aca           53

SEQ ID NO: 26            moltype = AA   length = 92
FEATURE                  Location/Qualifiers
REGION                   1..92
                         note = IGKV1-33*01/IGKV1D-33*01
source                   1..92
                         mol_type = protein
```

```
                        organism = synthetic construct
SEQUENCE: 26
DIQMTQSPSS LSASVGDRVT ITCQASQDIS NYLNWYQQKP GKAPKLLIYD ASNLETGVPS    60
RFSGSGSGTD FTFTISSLQP EDIATYYCQQ YD                                  92

SEQ ID NO: 27           moltype = DNA  length = 53
FEATURE                 Location/Qualifiers
misc_feature            1..53
                        note = IGKV1D-33*01
source                  1..53
                        mol_type = other DNA
                        organism = synthetic construct
SEQUENCE: 27
cacgaagctt gctaatggaa gccacgctcg tgcatggaag ggactatcgc aca            53

SEQ ID NO: 28           moltype = DNA  length = 57
FEATURE                 Location/Qualifiers
misc_feature            1..57
                        note = IGKV1-27*01
source                  1..57
                        mol_type = other DNA
                        organism = synthetic construct
SEQUENCE: 28
cacgaagcgt gtgttctgga agtacgctgc tgctgatggg tccactcatc cgcgcaa        57
```

ANTIBODIES AGAINST CARCINOEMBRYONIC ANTIGENS

CROSS REFERENCE TO RELATED APPLICATIONS

This application is a bypass continuation of PCT/US2022/079296, filed Nov. 4, 2022, which claims priority to U.S. Application No. 63/336,676, filed Apr. 29, 2022, and U.S. Application No. 63/275,998, filed Nov. 5, 2021, the entire contents of which are incorporated by reference herein for all purposes.

SEQUENCE LISTING

The present application contains a Sequence Listing which has been submitted electronically in XML format. Said XML copy, created on Jan. 26, 2023, is named "2022-11-02_01306-0001-00PCT-ST_26.xml" and is 37,116 bytes in size. The information in the electronic format of the sequence listing is incorporated herein by reference in its entirety.

DESCRIPTION

Field

The invention relates to monoclonal antibodies (mAbs) and antigen binding fragments thereof that bind carcinoembryonic antigen (also referred to herein as "CEA"). The invention thus encompasses these mAbs antibodies and in particular their uses for detecting CEA, and for diagnosing and treating diseases and conditions related to, or known to be associated with, aberrant CEA expression such as cancer.

Background

Carcinoembryonic antigen (CEA) belongs to a family of immunoglobulins with an approximate molecular weight of 180,500 Daltons (180 kDa). CEA is a protein that is present in certain tissues of a developing baby (fetus), but by the time a baby is born, its expression drops to a very low level. In adults, CEA is normally present at very low levels in the blood but may be elevated in certain types of cancer. CEA, also known as CEACAM5 or CD66e, was discovered in malignant tumors of endodermally derived epithelium of the gastrointestinal tract and pancreas (Gold et al. *The Journal of Experimental Medicine* 122:467-481 (1965)). Since the discovery of CEA nearly five decades ago, it has been revealed to be overexpressed in the majority of human carcinomas (Gold et al. *The Journal of Experimental Medicine* 122:467-481 (1965); Blumenthal et al. *BMC Cancer* 7:1-15 (2007)). The function of CEA is to transport iron from the intestine, reticuloendothelial system, and liver parenchymal cells to all proliferating cells in the body. CEA may also have a physiologic role as granulocyte/pollen-binding protein (GPBP) involved in the removal of certain organic matter and allergens from serum, and may have a further role in stimulating cell proliferation. Human CEA is described in the database UniProtKB/Swiss-Prot: P06731. CEA has immunoglobulin-like structural characteristics and many glycosylation modification sites (Beauchemin et al. *Cancer and Metastasis Reviews* 32:643-671 (2013)).

CEA can also be overexpressed in some non-cancer-related conditions, such as inflammation, cirrhosis, peptic ulcer, ulcerative colitis, rectal polyps, emphysema, and benign breast disease, and in smokers. For this reason, it is generally believed that detection of CEA will not be useful as a general cancer screening tool, but rather will have usefulness in evaluating response to cancer treatment. See, The Dynamic Monitoring of CEA in Response to Chemotherapy and Prognosis of MCRC Patients. Yu, et al. *BMC Cancer*. (2018) 18: 1076; and ASCO 2006 Update of Recommendations for the Use of Tumor Markers in Gastrointestinal Cancer. Gershon et al. *Journal of Clinical Oncology* (2006) 24: 5313. For example, when an individual has been diagnosed with cancer, an initial baseline test for CEA may be performed. Subsequent serial testing of CEA may be performed to monitor the cancer progression as the individual undergoes treatment and/or when the individual goes into remission. See, Roberto et al. *British Journal of Cancer* (2021) 124: 839.

BRIEF DESCRIPTION OF THE DRAWINGS

FIG. 2 displays a NCBI_Ig Blast Tool_IMGT view for the heavy chain of ADx-CEA. The single letter-coded amino-acid positions, CDR locations and the inclusion of gaps (*) to maximize homologies within human IgHVDJ are according to IMGT database. Nucleotide and predicted protein sequence is given below for heavy chain of V-D-J regions.

FIG. 3 displays a NCBI_Ig Tool_IMGT blast sample for the light chain of ADx-CEA. The single letter-coded amino-acid positions, CDR locations and the inclusion of gaps (*) to maximize homologies within human IgKVJ are according to IMGT database. Nucleotide and predicted protein sequence is given below for K chain of V-J regions.

FIG. 6A shows the phase-contrast image. FIG. 6B shows immunofluorescence staining.

FIG. 9A depicts sensitivity as compared to the Dako Omnis (Agilent) anti-CEA mAb (Clone II-7). FIG. 9B shows specificity as compared to the Dako antibody.

FIG. 10A depicts sensitivity as compared to the Dako Omnis (Agilent) anti-CEA mAb (Clone II-7). FIG. 10B shows specificity as compared to the Dako Omnis (Agilent) anti-CEA mAb (Clone II-7).

FIG. 11A depicts sensitivity as compared to the Dako Omnis (Agilent) anti-CEA mAb (Clone II-7). FIG. 11B shows specificity as compared to the Dako Omnis (Agilent) anti-CEA mAb (Clone II-7).

FIG. 12A depicts a representative low magnification image of colony formation in untreated BxPC-3 cells. FIG. 12B depicts a representative high magnification images of colony formation in ADx-CEA treated and untreated BxPC-3 cells. Picture of wells are representative of three independent experiments. FIG. 12C depicts the quantification of BxPC-3 colony numbers after ADx-CEA treatment.

FIG. 13A depicts results for pancreatic tissues. FIG. 13B depicts results for colon tissue. FIG. 13C depicts results for liver tissues.

DESCRIPTION OF THE EMBODIMENTS

I. Definitions

Figure 1:
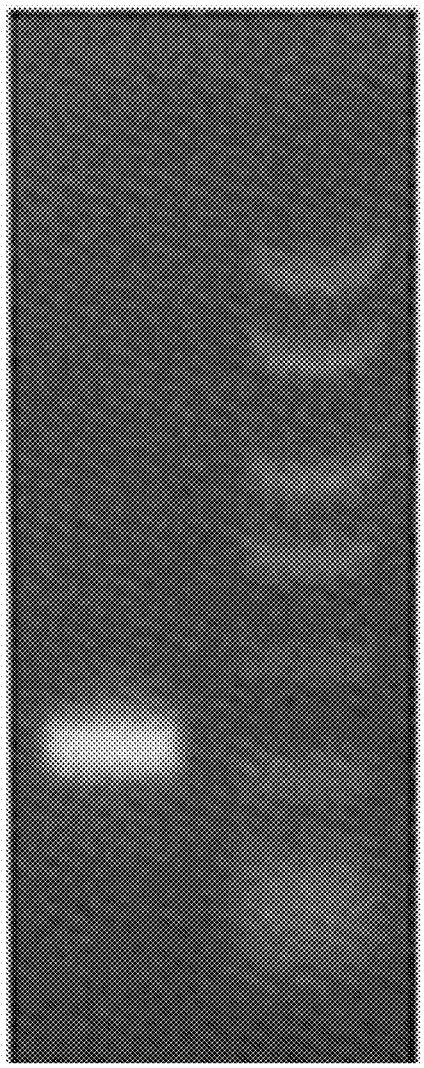
FIG. 1 shows the amplicon for the heavy chain of ADx-CEA.

In this application, the use of "or" means "and/or" unless stated otherwise. In the context of a multiple dependent claim, the use of "or" refers back to more than one preceding independent or dependent claim in the alternative only. The terms "comprising," "including," and "having" can be used interchangeably herein. According to the present invention, an "isolated" molecule is a molecule that has been removed from its natural milieu. As such, the term "isolated" does not necessarily reflect the extent to which the molecule has been purified.

As used herein, CEA is also known as Carcinoembryonic antigen-related cell adhesion molecule 5, CECAM5, Cell Adhesion Molecule 5, and CD66e. See, e.g., UniProtKB/Swiss-Prot: P06731.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. Recombinant, chimeric, and humanized antibodies are encompassed.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g., scFv); and multispecific antibodies formed from antibody fragments.

The term "antigen" refers to one or more molecules or one or more portions of a molecule capable of being bound by an antibody which is additionally capable of inducing an animal to produce an antibody capable of binding to an epitope of that antigen. An antigen can have one or more than one epitope. The specific reaction referred to above is meant to indicate that the antigen will react, in a highly preferential manner, with its corresponding antibody and not with the multitude of other antibodies which can be evoked by other antigens. The binding of antigen to antibody must be above background levels.

The term "cancer" is used herein to refer to a group of cells that exhibit abnormally high levels of proliferation and growth. A cancer may be benign (also referred to as a benign tumor), pre-malignant, or malignant. Cancer cells may be solid cancer cells or leukemic cancer cells.

The term "complementarity determining region, or CDR" refers to amino acid sequences which together define the binding affinity and specificity of the natural Fv region of a native immunoglobulin binding site. The light and heavy chains of an immunoglobulin each have three CDRs.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ, respectively.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, Fifth Edition, NIH Publication 91-3242, Bethesda MD (1991), vols. 1-3. In some embodiments, for the VL, the subgroup is subgroup kappa I as in Kabat et al., supra. In some embodiments, for the VH, the subgroup is subgroup III as in Kabat et al., supra.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3).

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., J. Chromatogr. B 848:79-87 (2007).

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The "stages" of pancreatic cancer refer to the American Joint Committee on Cancer (AJCC) clinical stages: 0, IA, IB, IIA, IIB, III, and IV, as defined in American Joint Committee on Cancer. Exocrine Pancreas. In: *AJCC Cancer Staging Manual.* 8$^{th}$ ed. New York, NY: Springer; 2017:337. As used herein, "early stage" pancreatic cancer refers to stages I and II, and "late stage" pancreatic cancer refers to Stages III and IV.

As used herein, "negative control" with respect to assays and detections referred to herein refers to a control that is normally used in the field by experts for the type of assay and type of cancer being detected or assayed. In one example of detection of CEA levels in human blood, a normal blood (plasma or serum) CEA level may be approximately 0-2.5 ng/mL. If the level of CEA detected is higher than this level, the level may be said to be higher than the negative control.

II. Compositions and Methods

Anti-CEA antibodies, antibody fragments, monoclonal antibodies, antibody conjugates, compositions comprising the described antibodies and methods of their use are provided.

A. EXEMPLARY ANTI-CEA ANTIBODIES

The Sequence Table below provides the sequences of the antibody disclosed and claimed herein (ADx-CEA). See, SEQ ID Nos: 1-12.

Provided herein are antibodies and antibody fragments that bind specifically to human CEA, including ADx-CEA and fragments and variants thereof.

In certain embodiments, an anti-CEA antibody and antibody fragments are provided comprising a heavy chain variable region ("VH") comprising VH CDR1, CDR2 and CDR3 comprising SEQ ID NOs: 1, 2 and 3 respectively, and a light chain variable region ("VL") comprising VL CDR1, CDR2, and/or CDR3 of any one of SEQ ID NOs: 4, 5 and 6 respectively.

In some embodiments, antibodies comprising the following are provided:
 (a) HCDR1 comprising the amino acid sequence of SEQ ID NO: 1; (b) HCDR2 comprising the amino acid sequence of SEQ ID NO: 2; (c) HCDR3 comprising the amino acid sequence of SEQ ID NO: 3; with or without (d) LCDR1 comprising the amino acid sequence of SEQ ID NO: 4; (e) LCDR2 comprising the amino acid sequence of SEQ ID NO: 5; and (f) LCDR3 comprising the amino acid sequence of SEQ ID NO: 6; or
 (b) a heavy chain variable region (VH) and a light chain variable region (VL), wherein: the VH is at least 90%, 91%, 92%, 93%, 94%, 95%, 96%, 97%, 98%, 99%, or 100% identical to the amino acid sequence of SEQ ID NO: 7 and the VL is at least 90%, 91%, 92%, 93%, 94%, 95%, 96%, 97%, 98%, 99%, or 100% identical to the amino acid sequence of SEQ ID NO: 8; or
 (c) a heavy chain variable region (VH) and a light chain variable region (VL), wherein the VH comprises the amino acid sequence of SEQ ID NO: 7 and the VL comprises the amino acid sequence of SEQ ID NO: 8; or
 (d) HCDR1 comprising the amino acid sequence of SEQ ID NO: 1; (b) HCDR2 comprising the amino acid sequence of SEQ ID NO: 2; (c) HCDR3 comprising the amino acid sequence of SEQ ID NO: 3; with or without (d) LCDR1 comprising the amino acid sequence of SEQ ID NO: 4; (e) LCDR2 comprising the amino acid sequence of SEQ ID NO: 5; and (f) LCDR3 comprising the amino acid sequence of SEQ ID NO: 6; and a heavy chain variable region (VH) and a light chain variable region (VL), wherein: the VH is at least 90%, 91%, 92%, 93%, 94%, 95%, 96%, 97%, 98%, 99%, or 100% identical to the amino acid sequence of SEQ ID NO: 7 and the VL is at least 90%, 91%, 92%, 93%, 94%, 95%, 96%, 97%, 98%, 99%, or 100% identical to the amino acid sequence of SEQ ID NO: 8.

In some embodiments, the isolated antibody or antibody fragment described herein is a monoclonal antibody. In further embodiments, the isolated antibody or antibody fragment is a fully human antibody. In some embodiments, the isolated antibody or antibody fragment is an antibody fragment. In a further embodiment, the antibody fragment is a Fab, Fab', Fv, scFv or (Fab')$_2$. In some embodiments, the isolated antibody or antibody fragment is a full-length antibody. In some embodiments, the isolated antibody or antibody fragment comprises an Fc region, wherein the Fc region of the antibody comprises IgG1, IgG2, IgG3, IgG4, IgG4.1 or IgG4.2.

In some embodiments, a composition is provided comprising an antibody or antibody fragment and a pharmaceutically acceptable carrier.

In some embodiments, the isolated antibody or antibody fragment is immobilized on a solid phase. In some embodiments, the isolated antibody or antibody fragment is detectably labeled. In some embodiments, the isolated antibody or antibody fragment is conjugated to a cytotoxic radionuclide.

In some embodiments, the isolated antibody or antibody fragment is conjugated to a cytotoxic drug. In some embodiments, the isolated antibody or antibody fragment is conjugated to a cytotoxic protein.

In some embodiments, an isolated DNA sequence is provided which encodes the antibody or antibody fragment. In some embodiments, the DNA comprises SEQ ID NO: 11, or a fragment thereof. In some embodiments, the DNA comprises SEQ ID NO: 12, or a fragment thereof. In some embodiments, the DNA comprises SEQ ID NO: 11, or a fragment thereof and SEQ ID NO: 12, or a fragment thereof. In some embodiments, the DNA comprises a sequence that is at least 90%, 91%, 92%, 93%, 94%, 95%, 96%, 97%, 98%, 99%, or 100% identical to SEQ ID NO: 11, or a fragment thereof. In some embodiments, the DNA comprises a sequence that is at least 90%, 91%, 92%, 93%, 94%, 95%, 96%, 97%, 98%, 99%, or 100% identical to SEQ ID NO: 12, or a fragment thereof. In some embodiments, the DNA comprises SEQ ID NO: 11, or a fragment thereof and SEQ ID NO: 12, or a fragment thereof. In some embodiments, the DNA comprises a sequence that is at least 90%, 91%, 92%, 93%, 94%, 95%, 96%, 97%, 98%, 99%, or 100% identical to SEQ ID NO: 11, or a fragment thereof and a sequence that is at least 90%, 91%, 92%, 93%, 94%, 95%, 96%, 97%, 98%, 99%, or 100% identical to SEQ ID NO: 12, or a fragment thereof.

In some embodiments, a vector is provided comprising the DNA sequence which encodes the antibody or antibody fragment.

In some embodiments, a host cell transformed with the vector comprising the DNA sequence which encodes the antibody or antibody fragment is provided for.

In some embodiments, a process is provided for the production of an antibody, comprising culturing the host cell transformed with the vector comprising the DNA sequence which encodes the antibody or antibody fragment, and isolating the antibody molecule.

In certain embodiments, an anti-CEA antibody or antibody fragment comprises an isolated antibody comprising a VH that is at least 90%, 91%, 92%, 93%, 94%, 95%, 96%, 97%, 98%, 99%, or 100% identical to the amino acid sequence of SEQ ID NO: 7 and a VL that is at least 90%, 91%, 92%, 93%, 94%, 95%, 96%, 97%, 98%, 99%, or 100% identical to the amino acid sequence of SEQ ID NO: 8. In some embodiments, this antibody comprises HCDR1 comprising the amino acid sequence of SEQ ID NO: 1; (b) HCDR2 comprising the amino acid sequence of SEQ ID NO: 2; and (c) HCDR3 comprising the amino acid sequence of SEQ ID NO: 3; with or without (d) LCDR1 comprising the amino acid sequence of SEQ ID NO: 4; (e) LCDR2 comprising the amino acid sequence of SEQ ID NO: 5; and (f) LCDR3 comprising the amino acid sequence of SEQ ID NO: 6.

In some embodiments, the invention comprises a method of treating cancer comprising administering a therapeutically effective amount of the anti-CEA antibody or antibody fragment described herein, or a composition thereof, or the DNA or vector thereof, to a subject in need thereof. In some embodiments the cancer is a solid tumor. In some embodiments the cancer is a leukemia. In some embodiments, the cancer is colorectal cancer, liver cancer, stomach cancer, ovarian cancer, thyroid cancer, lung cancer, breast cancer, or pancreatic cancer.

In certain embodiments, an immunoassay is provided for detecting a CEA antigen comprising: (a) contacting said sample with an effective binding amount of an antibody or antibody fragment as described herein, such as ADx-CEA; and (b) detecting said antigen by detecting the binding of the antibody to the CEA antigen. In some embodiments, the assay is used to detect cancer cells expressing a CEA antigen. In some embodiments, the assay is used to detect a solid tumor. In further embodiments, the cancer is colorectal cancer, liver cancer, stomach cancer, ovarian cancer, thyroid cancer, lung cancer, breast cancer, or pancreatic cancer.

In some embodiments, the invention comprises a method of detecting cancer in a subject comprising contacting the antibody or antibody fragment described herein to a sample isolated from a subject having or suspected of having cancer. In some embodiments, the cancer is a solid tumor. In further embodiments, the solid tumor is colorectal cancer, liver cancer, stomach cancer, ovarian cancer, thyroid cancer, lung cancer, breast cancer, or pancreatic cancer.

In certain embodiments, the invention provides a kit for the immunohistochemical detection of a solid tumor cancer comprising cells expressing a CEA antigen comprising: (a) an antibody or antibody fragment as described herein such as ADx-CEA; and (b) a secondary antibody conjugated to a detectable label, wherein the secondary antibody binds to and is capable of detecting the antibody of (a) when bound to a CEA antigen. Alternatively, the secondary antibody is not conjugated to a detectable label, and instead, a label that binds to or interacts with the secondary antibody is used for detection. Methods of detecting CEA using said kit are encompassed.

In some embodiments, the invention is a method for determining the status of a solid tumor cancer in a subject comprising: (a) removing a sample from a subject having a solid tumor cancer; (b) contacting the sample with the antibody or antibody fragment as described herein such as ADx-CEA, thereby forming a complex between a CEA antigen and the antibody or antibody fragment; (c) labeling the specimen with a label specific for the antigen-antibody complex; and (d) detecting the presence of the antigen-antibody complex by detecting the label. In some embodiments, the sample is blood, including whole blood, serum, or plasma, or a tissue or cell.

In some embodiments, the steps (a) through (d) described herein are repeated at a later time point. In some embodiments, the time point is after the subject has started therapy. In some embodiments, the time point is after the subject has started a new or second (co-) therapy. In some embodiments, the solid tumor cancer is colorectal cancer, liver cancer, stomach cancer, ovarian cancer, thyroid cancer, lung cancer, breast cancer, or pancreatic cancer. In some embodiments, the solid tumor cancer is pancreatic cancer. In some embodiments, the subject has been diagnosed with cancer and is receiving, or will receive, a therapy. In some embodiments, the sample is isolated from the subject prior to the start of therapy. In some embodiments, the sample is isolated from the subject after the start of therapy. In some embodiments, the therapy is chemotherapy or radiation. In some embodiments, the chemotherapy is Erlotinib, Fluorouracil, or Oxaliplatin. In some embodiments, the therapy is surgery, including a whipple procedure, distal pancreatectomy, and a total pancreatectomy, radiation therapy, proton beam therapy, stereotactic body radiation (SBRT) or cyberknife, immunotherapy, targeted therapy or chemotherapy.

In some embodiments, the invention comprises a method for determining the status of a solid tumor cancer in a subject described herein, wherein the level of CEA is determined, wherein a level of CEA that is higher at the later time point is indicative that the therapy is not fully effective, and wherein a level of CEA antigen that is the same or lower at the later time point is indicative that the therapy is at least partially effective. In some embodiments, the subject is in remission. In some embodiments, the method described herein is repeated at a later time point after the subject is in remission, wherein the level of CEA is determined, wherein a level of CEA that is higher at the later time point is indicative the cancer is no longer in remission, and wherein a level of CEA that is the same or lower at the later time point is indicative that the cancer continues to be in remission. In some embodiments, the method is a replacement for computed tomography.

In certain embodiments, the invention comprises a method for detecting cancers characterized by the expression of gene products of CEA and homologues thereof, comprising the steps of: (a) identifying gene products expressed by CEA and homologues thereof in a human patient having cancer by isolating a biological sample from the subject, wherein the sample is one that would comprise CEA gene product if the CEA gene were expressed, (b) utilizing said gene products as biomarkers by contacting the biological sample with the anti-CEA antibody or antibody fragment described herein such as ADx-CEA, or the composition thereof, to create a sample-antibody complex, (c) removing any unbound antibody and then contacting the sample-antibody complex with a label specific for the antibody or sample-antibody complex; and (d) detecting the presence of the antigen-antibody complex by detecting the label, wherein detection of the label indicates detection of cancer.

In some embodiments, the invention provides a method of determining the status of a cell in a sample comprising: (a) obtaining said sample from a subject; contacting said sample with the antibody or antibody fragment of as described herein such as ADx-CEA, or the composition thereof; and (c) determining the quantity of CEA detected by the antibody or antibody fragment.

In some embodiments, the invention provides a method for detecting pancreatic cancer in a patient comprising (a) removing a pancreatic or blood specimen from a patient suspected of or having pancreatic cancer; (b) contacting the specimen with an antibody or antibody fragment as described herein, or the composition thereof, thereby forming antigen-antibody complexes in said specimen; (c) labeling the specimen with a label specific for the antibody or antigen-antibody complex; (d) detecting the presence of the antigen-antibody complex by detecting the label; and (e) determining the level of CEA antigen as compared to a negative control, wherein a level of CEA antigen that is greater than the negative control is indicative of pancreatic cancer. In some embodiments, the method is performed in vitro. In further embodiments, the pancreatic cancer is early stage, and the method is capable of detecting CEA antigen at this early stage. In further embodiments, the pancreatic cancer is in stage I, II, IIA, or IIB, and the method is capable of detecting CEA antigen at this early stage. In some embodiments, the pancreatic cancer is at stage II, IIA, or IIB.

In some embodiments, the invention provides a kit for the detection of cancer comprising: (a) an antibody or antibody fragment having heavy chain CDR1, CDR2 and CDR3 sequences comprising SEQ ID NOs: 1, 2 and 3, respectively, and light chain CDR1, CDR2 and CDR3 sequences comprising SEQ ID NOs: 4, 5 and 6, respectively; and (b) a secondary antibody conjugated to a detectable label or a separate non-conjugated detectable label that binds to the secondary antibody, the antibody-antigen complex, or the monoclonal antibody of (a). In some embodiments, the kit is for the immunohistochemical detection of pancreatic cancer.

In some embodiments, the invention comprises a immunohistochemical method of detecting cancer in a tissue specimen collected from patients comprising the steps of: (a) obtaining a tissue specimen; (b) contacting said tissue specimen with the antibody of antibody fragment described herein, or the composition thereof; (c) after step (b), contacting the tissue specimen with a detectable label that binds to the secondary antibody, the antibody-antigen complex, or the antibody; and (d) staining said tissue specimen with an immunohistochemical staining; wherein said staining indicates antibody binding and presence of cancer in said tissue specimen. In some embodiments the cancer is pancreatic.

In some embodiments, a composition comprising: a tissue, cell, or blood specimen, and an antibody-antigen complex between the antibody or antibody fragment described herein, or the composition thereof and CEA antigen in the tissue, cell, or blood sample, wherein said sample is from a patient suffering from cancer is provided. In certain embodiments, the cancer is colorectal cancer, liver cancer, stomach cancer, ovarian cancer, thyroid cancer, lung cancer, breast cancer, or pancreatic cancer.

In some embodiments, a use of the antibody or antibody fragment described herein, or the composition thereof, for detecting cancer is provided. In further embodiments, the cancer is colorectal cancer, liver cancer, stomach cancer, ovarian cancer, thyroid cancer, lung cancer, breast cancer, or pancreatic cancer.

In some embodiments, a method for monitoring progression of cancer and/or therapeutic efficacy of a cancer therapeutic is provided comprising (a) obtaining an initial sample from a human patient with cancer at a first time point; (b) contacting said sample with an antibody or antibody fragment as described herein, or the composition thereof, forming an antigen-antibody complex; (c) labeling the specimen with a label specific for the antigen-antibody complex; and (d) detecting the presence of the antigen-antibody complex by detecting the label; (e) determining the level of CEA antigen detected by the antibody or antibody fragment to determine a baseline level of CEA antigen associated with the patient's cancer; (f) obtaining a second sample at a second (later) timepoint, optionally wherein the second timepoint is after a period of time whereby the subject has been receiving therapy; (g) repeating steps (b) through (e) to determine a second level of CEA antigen associated with the patient's cancer; and (h) determining that the patient's cancer has progressed if the level of CEA antigen at the second timepoint is greater than the level at baseline; and determining that the patient's cancer has regressed if the level of CEA antigen at the second timepoint is less than the level at baseline. In some embodiments, the cancer is colorectal cancer, liver cancer, stomach cancer, ovarian cancer, thyroid cancer, lung cancer, breast cancer, or pancreatic cancer. In some embodiments, the solid tumor cancer is pancreatic cancer. In some embodiments, an increase in the CEA at the second time point is indicative of progression of the cancer. In some embodiments, a decrease in the CEA at the second time point is indicative of regression of the cancer. In some embodiments, the first timepoint is before therapy or at initial diagnosis. In some embodiments, the first timepoint is after therapy or at initial diagnosis. In some embodiments, the second timepoint is after receiving therapy. In some embodiments, the method is performed in vitro. In some embodiments, the therapy is surgery, including a whipple procedure, distal pancreatectomy, and a total pancreatectomy, radiation therapy, proton beam therapy, stereotactic body radiation (SBRT) or cyberknife, immunotherapy, targeted therapy and chemotherapy.

B. GLYCOSYLATION VARIANTS

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn297 (e. g. complex, hybrid and high mannose structures) as measured by MALDI-TOF mass spectrometry, as described in WO 2008/077546, for example. "Asn297" refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. J. Mol. Biol. 336:1239-1249 (2004); Yamane-Ohnuki et al. Biotech. Bioeng. 87: 614 (2004). Examples of cell lines capable of producing defucosylated antibodies include Lec13 CHO cells deficient in protein fucosylation (Ripka et al. Arch. Biochem. Biophys. 249: 533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. Biotech. Bioeng. 87: 614 (2004); Kanda, Y. et al., Biotechnol. Bioeng., 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

C. FC REGION VARIANTS

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important, yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, Annu. Rev. Immunol. 9:457-492 (1991). Non-limiting examples of in vitro assays to assess ADCC activity of a molecule of interest is described in U.S. Pat. No. 5,500,362 (see, e.g. Hellstrom, I. et al. Proc. Nat'l Acad. Sci. USA 83:7059-7063 (1986)) and Hellstrom, I et al., Proc. Nat'l Acad. Sci. USA 82:1499-1502 (1985); 5,821,337 (see Bruggemann, M. et al., J. Exp. Med. 166:1351-1361 (1987)). Alternatively, non-radioactive assays methods may be employed (see, for example, ACTI™ non-radioactive cytotoxicity assay for flow cytometry (CellTechnology, Inc. Mountain View, CA; and CytoTox 96® non-radioactive cytotoxicity assay (Promega, Madison, WI). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., J. Immunol. Methods 202:163 (1996); Cragg, M. S. et al., Blood 101:1045-1052 (2003); and Cragg, M. S. and M. J. Glennie, Blood 103:2738-2743 (2004)). FcRn binding and in vivo clearance/half-life determinations can also be performed using methods known in the art (see, e.g., Petkova, S. B. et al., Int'l. Immunol. 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields et al., J. Biol. Chem. 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. J. Immunol. 164: 4178-4184 (2000).

Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 252, 254, 256, 265, 272, 286, 303, 305, 307, 311, 312, 317, 340, 356, 360, 362, 376, 378, 380, 382, 413, 424 or 434, e.g., substitution of Fc region residue 434 (e.g., U.S. Pat. No. 7,371,826).

See also Duncan & Winter, Nature 322:738-40 (1988); U.S. Pat. Nos. 5,648,260; 5,624,821; and WO 94/29351 concerning other examples of Fc region variants.

In some embodiments, an antibody is provided according to the Table of Sequences, wherein the isotype is human IgG1. In some embodiments, an antibody is provided according to the Table of Sequences, wherein the isotype is human IgG2. In some embodiments, an antibody is provided according to the Table of Sequences, wherein the isotype is human IgG3. In some embodiments, an antibody is provided according to the Table of Sequences, wherein the isotype is human IgG4.

TABLE 1

Table of Sequences

| Name | Amino Acid Sequence | SEQ ID NO. |
| --- | --- | --- |
| HCDR1 | GFSLTSNG | 1 |
| HCDR2 | IWAGGNT | 2 |
| HCDR3 | ARDDGYYYAMDY | 3 |
| LCDR1 | QDINKY | 4 |
| LCDR2 | YTS | 5 |
| LCDR3 | LQYDNT | 6 |
| VH | EVQLEESGPGLVAPSQSLSITCTVSGFSLTSNGVHWVR QPPGKGLEWLGIIWAGGNTNYNSALMSRLSIGKDNSKS QVFLKMNSLQTDDTAMYYCAR* | 7 |
| VL | DILMTQSPSSLSASLGGTVTITCKASQDINKYIAWYQH KPGKGPRLLIHYTSTLQPAIPSRFSGSGSGRDYSFSIS NLEPEDIATYYCLQYD** | 8 |
| Full Heavy V-D-J-REGION | EVQLEESGPGLVAPSQSLSITCTVSGFSLTSNGVHWVR QPPGKGLEWLGIIWAGGNTNYNSALMSRLSIGKDNSKS QVFLKMNSLQTDDTAMYYCARDDGYYYAMDYWGQGTTV TR | 9 |
| Full Light V-J-REGION | DILMTQSPSSLSASLGGTVTITCKASQDINKYIAWYQH KPGKGPRLLIHYTSTLQPAIPSRFSGSGSGRDYSFSIS NLEPEDIATYYCLQYDNTFDAGTKLEIK | 10 |
| Nucleotide Sequence Heavy Chain | tgaggtgcagctggaggagtcaggacctggcctggtgg cgccctcacagagcctgtccatcacttgcactgtctct gggttttcattaaccagcaatggtgtacactgggttcg ccagcctccaggaaagggtctggagtggctgggaataa tatgggctggtggaaacacaaattataattcggctctc atgtccagactgagcatcggcaaagacaactccaagag tcaagttttcttaaaaatgaacagtctgcaaactgatg acacagccatgtactactgtgccagagatgatggttac tactatgctatggactactggggccaagggaccacggt cac | 11 |
| Nucleotide Sequence Light Chain | gacattctgatgacccagtctccatcctcactgtctgc atctctgggaggcacagtcaccatcacttgcaaggcga gccaggacataaacaagtatatagcttggtaccaacac aagcctggaaaaggtcctaggctgctcatacattacac atctacattacagccagccatcccatcaaggttcagtg gaagtgggtctggagagattattccttcagcatcagc aacctggagcctgaagatattgcaacttattattgtct acagtatgataacacgttcgatgctgggaccaagctgg aaataaa | 12 |

TABLE 1-continued

Table of Sequences

| Name | Amino Acid Sequence | SEQ ID NO. |
|---|---|---|
| VH Primer Sequence | tgaggtgcagctggaggagtc | 13 |
| JH Primer Sequence | gtgaccgtggtccttggccccag | 14 |
| VK Primer Sequence | gacattctgatgacccagtct | 15 |
| JK Prime Sequence | ttttatttccagcttggtccc | 16 |

*HCDR3 is not present in this representation of VH because of the process of sequencing. HCDR3 is present, however, and is shown in the representation of the full heavy chain.
**LCDR3 is not present in this representation of VL because of the process of sequencing. HCDR3 is present, however, and is shown in the representation of the full heavy chain.

D. CYSTEINE ENGINEERED ANTIBODY VARIANTS

In certain embodiments, it may be desirable to create cysteine engineered antibodies, e.g., "thioMantibodies," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

E. ANTIBODY DERIVATIVES

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In some embodiments, the nonproteinaceous moiety is a carbon nanotube (Kam et al., Proc. Natl. Acad. Sci. USA 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

F. RECOMBINANT METHODS

Antibodies may be produced using recombinant methods and compositions, e.g., as described in U.S. Pat. No. 4,816, 567. In some embodiments, isolated nucleic acid encoding an anti-CEA antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In some embodiments, the host cell is eukaryotic, e.g. a Chinese Hamster Ovary (CHO) cell or lymphoid cell (e.g., Y0, NS0, Sp20 cell). In some embodiments, a method of making an anti-CEA antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-CEA antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, *Methods in Molecular Biology*, Vol. 248 (B. K. C. Lo, ed., Humana Press, Totowa, N J, 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., *Annals N.Y. Acad. Sci.* 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, Methods in Molecular Biology, Vol. 248 (B. K. C. Lo, ed., Humana Press, Totowa, NJ), pp. 255-268 (2003).

G. IMMUNOCONJUGATES

The invention also provides immunoconjugates comprising an anti-CEA antibody herein conjugated to one or more other therapeutic agents or radioactive isotopes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or 1123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis (p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, IL., U.S.A).

H. PHARMACEUTICAL FORMULATIONS AND COMPOSITIONS

Pharmaceutical formulations or compositions of an anti-CEA antibody as described herein are prepared by mixing such antibody having the desired degree of purity with one or more optional pharmaceutically acceptable carriers, diluents, and/or excipients (*Remington's Pharmaceutical Sciences* 16th edition, Osol, A. Ed. (1980)), in the form of lyophilized formulations or aqueous solutions. Pharmaceutically acceptable carriers, diluents, and excipients are generally nontoxic to recipients at the dosages and concentrations employed, and include, but are not limited to: sterile water, buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation or composition herein may also contain more than one active ingredients as necessary for the particular indication being treated, preferably those with complementary activities that do not adversely affect each other. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations or compositions to be used for in vivo administration are generally sterile. Sterility may be readily accomplished, e.g., by filtration through sterile filtration membranes.

I. EMBODIMENTS

The following embodiments are provided:

Embodiment 1. An isolated antibody or antibody fragment comprising, an (a) HCDR1 comprising the amino acid sequence of SEQ ID NO: 1; (b) HCDR2 comprising the amino acid sequence of SEQ ID NO: 2; (c) HCDR3 comprising the amino acid sequence of SEQ ID NO: 3; (d) LCDR1 comprising the amino acid sequence of SEQ ID NO: 4; (e) LCDR2 comprising the amino acid sequence of SEQ ID NO: 5; and (f) LCDR3 comprising the amino acid sequence of SEQ ID NO: 6.

Embodiment 2. The isolated antibody of embodiment 1, wherein the antibody comprises a heavy chain variable region ($V_H$) and a light chain variable region ($V_L$), wherein: the $V_H$ is at least 90%, 91%, 92%, 93%, 94%, 95%, 96%, 97%, 98%, 99%, or 100% identical to the amino acid sequence of SEQ ID NO: 7 and the $V_L$ is at least 90%, 91%, 92%, 93%, 94%, 95%, 96%, 97%, 98%, 99%, or 100% identical to the amino acid sequence of SEQ ID NO: 8.

Embodiment 3. The isolated antibody of embodiment 1 or embodiment 2, wherein the antibody comprises a heavy chain variable region ($V_H$) and a light chain variable region ($V_L$), wherein the $V_H$ comprises the amino acid sequence of SEQ ID NO: 7 and the $V_L$ comprises the amino acid sequence of SEQ ID NO: 8.

Embodiment 4. An isolated antibody or antibody fragment comprising, an (a) HCDR1 comprising the amino acid sequence of SEQ ID NO: 1; (b) HCDR2 comprising the amino acid sequence of SEQ ID NO: 2; (c) HCDR3 comprising the amino acid sequence of SEQ ID NO: 3; (d) LCDR1 comprising the amino acid sequence of SEQ ID NO: 4; (e) LCDR2 comprising the amino acid sequence of SEQ ID NO: 5; and (f) LCDR3 comprising the amino acid sequence of SEQ ID NO: 6, and a heavy chain variable region ($V_H$) and a light chain variable region ($V_L$), wherein: the $V_H$ is at least 90%, 91%, 92%, 93%, 94%, 95%, 96%, 97%, 98%, 99%, or 100% identical to the amino acid sequence of SEQ ID NO: 7 and the $V_L$ is at least 90%, 91%, 92%, 93%, 94%, 95%, 96%, 97%, 98%, 99%, or 100% identical to the amino acid sequence of SEQ ID NO: 8.

Embodiment 5. The isolated antibody or antibody fragment of any one of the preceding embodiments, wherein the antibody is a monoclonal antibody.

Embodiment 6. The isolated antibody or antibody fragment of any one of the preceding embodiments, wherein the antibody is a fully human antibody.

Embodiment 7. The isolated antibody or antibody fragment of any one of the preceding embodiments, wherein the antibody is an antibody fragment.

Embodiment 8. The isolated antibody or antibody fragment of embodiment 7, wherein the fragment is a Fab, Fab', Fv, scFv or (Fab')$_2$.

Embodiment 9. The isolated antibody or antibody fragment of any one of embodiments 1-5, wherein the antibody is a full-length antibody.

Embodiment 10. The isolated antibody or antibody fragment of any one of embodiments 1-9, wherein the Fc region of the antibody, if present, comprises IgG1, IgG2, IgG3, IgG4, IgG4.1 or IgG4.2.

Embodiment 11. A composition comprising the antibody or antibody fragment of any one of embodiments 1-10 and a pharmaceutically acceptable carrier.

Embodiment 12. The isolated antibody or antibody fragment of any one of embodiments 1-10, immobilized on a solid phase.

Embodiment 13. The isolated antibody or antibody fragment of any one of embodiments 1-10, which is detectably labeled.

Embodiment 14. The isolated antibody or antibody fragment of any one of embodiments 1-10, conjugated to a cytotoxic radionuclide.

Embodiment 15. The isolated antibody or antibody fragment of any one of embodiments 1-10, conjugated to a cytotoxic drug.

Embodiment 16. The isolated antibody or antibody fragment of any one of embodiments 1-10, conjugated to a cytotoxic protein.

Embodiment 17. An isolated DNA sequence encoding the antibody or antibody fragment of any one of embodiments 1-10.

Embodiment 18. The DNA of embodiment 17, comprising SEQ ID NO: 11 or a fragment thereof, or a sequence that is at least 80, 90, or 95% identical to SEQ ID NO: 11.

Embodiment 19. The DNA of embodiment 17, comprising SEQ ID NO: 12 or a fragment thereof, or a sequence that is at least 80, 90, or 95% identical to SEQ ID NO: 12.

Embodiment 20. The DNA of embodiment 17, comprising SEQ ID NO: 11 or a fragment thereof and SEQ ID NO: 12 or a fragment thereof, or comprising a sequence that is at least 80, 90, or 95% identical to SEQ ID NO: 11 and a sequence that is at least 80, 90, or 95% identical to SEQ ID NO: 12.

Embodiment 21. A vector comprising the DNA sequence of any one of embodiments 17-20.

Embodiment 22. A host cell transformed with the vector of embodiment 21.

Embodiment 23. A process for the production of an antibody, comprising culturing the host cell of embodiment 22 and isolating the antibody molecule.

Embodiment 24. An isolated antibody comprising a $V_H$ that is at least 90%, 91%, 92%, 93%, 94%, 95%, 96%, 97%, 98%, 99%, or 100% identical to the amino acid sequence of SEQ ID NO: 7 and a $V_L$ that is at least 90%, 91%, 92%, 93%, 94%, 95%, 96%, 97%, 98%, 99%, or 100% identical to the amino acid sequence of SEQ ID NO: 8.

Embodiment 25. A method of treating cancer comprising administering a therapeutically effective amount of the anti-CEA antibody of any one of claim 1-10, or 14-16, the composition of claim 11, or the DNA or vector of any one of claims 17-21 to a subject in need thereof.

Embodiment 26. An immunoassay for detecting a CEA antigen comprising: (a) contacting said sample with an effective binding amount of the antibody or antibody fragment according to any one of embodiments 1-10; and (b) detecting said antigen by detecting the binding of the antibody to the CEA antigen.

Embodiment 27. The immunoassay of embodiment 26, wherein the assay is used to detect cancer cells expressing a CEA antigen.

Embodiment 28. The immunoassay of embodiment 26, wherein the assay is used to detect a solid tumor.

Embodiment 29. The immunoassay of embodiment 27 or 28, wherein the cancer is colorectal cancer, liver cancer, stomach cancer, ovarian cancer, thyroid cancer, lung cancer, breast cancer, or pancreatic cancer.

Embodiment 30. A method of detecting cancer in a subject comprising contacting the antibody of any one of embodiments 1-10 to a sample isolated from a subject having or suspected of having cancer.

Embodiment 31. The method of embodiment 30, wherein the cancer is a solid tumor.

Embodiment 32. The method of embodiment 30, wherein the solid tumor is colorectal cancer, liver cancer, stomach cancer, ovarian cancer, thyroid cancer, lung cancer, breast cancer, or pancreatic cancer.

Embodiment 33. A kit for the immunohistochemical detection of a solid tumor cancer comprising cells expressing a CEA antigen comprising: (a) an antibody according to any one of embodiments 1-10; and (b) a secondary antibody conjugated to a detectable label, wherein the secondary antibody binds to and is capable of detecting the antibody of (a) when bound to a CEA antigen.

Embodiment 34. A method for determining the status of a solid tumor cancer in a subject comprising: (a) removing a sample from a subject having a solid tumor cancer; (b) contacting the sample with the antibody or antibody fragment of any one of embodiments 1-10, thereby forming a complex between a CEA antigen and the antibody or antibody fragment; (c) labeling the specimen with a label specific for the antigen-antibody complex; and (d) detecting the presence of the antigen-antibody complex by detecting the label.

Embodiment 35. The method of embodiment 34, wherein the solid tumor cancer is colorectal cancer, liver cancer, stomach cancer, ovarian cancer, thyroid cancer, lung cancer, breast cancer, or pancreatic cancer.

Embodiment 36. The method of embodiment 34, wherein the solid tumor cancer is pancreatic cancer.

Embodiment 37. The method of any one of embodiments 34-36, wherein the subject has been diagnosed with cancer and is receiving, or will receive, a therapy.

Embodiment 38. The method of embodiment 37, wherein the sample is isolated from the subject prior to the start of therapy.

Embodiment 39. The method of embodiment 37, wherein the sample is isolated from the subject after the start of therapy.

Embodiment 40. The method of any one of embodiments 34-39, further comprising repeating steps (a) through (d) at a later time point.

Embodiment 41. The method of embodiment 40, wherein the later time point is after the subject has started therapy.

Embodiment 42. The method of embodiment 40, wherein the later time point is after the subject has started a new or second (co-) therapy.

Embodiment 43. The method of any one of embodiments 41-42, wherein the therapy is chemotherapy or radiation.

Embodiment 44. The method of claim 43, wherein the chemotherapy is Erlotinib, Fluorouracil, or Oxaliplatin.

Embodiment 45. The method of any one of claims 41-42, wherein the therapy is surgery, including a whipple procedure, distal pancreatectomy, and a total pancreatectomy, radiation therapy, proton beam therapy, stereotactic body radiation (SBRT) or cyberknife, immunotherapy, targeted therapy or chemotherapy.

Embodiment 46. The method of any one of embodiments 34-45, wherein the level of CEA antigen detected is determined, wherein a level of CEA that is higher at the later time point is indicative that the therapy is fully effective, and wherein a level of CEA antigen that is the same or lower at the later time point is indicative that the therapy is at least partially effective.

Embodiment 47. The method of any one of embodiments 34-46, wherein the subject is in remission.

Embodiment 48. The method of embodiment 47, further comprising repeating steps (a) through (d) at a later time point after the subject is in remission, wherein the level of CEA is determined, wherein a level of CEA that is higher at the later time point is indicative the cancer is no longer in remission, and wherein a level of CEA that is the same or lower at the later time point is indicative that the therapy continues to be in remission.

Embodiment 49. The method of any one of embodiments 34-48, wherein the sample is blood, including whole blood, serum, or plasma, tissue or cell.

Embodiment 50. The method of any one of embodiments 34-49, wherein the method is a replacement for computed tomography.

Embodiment 51. A method for detecting cancers characterized by the expression of gene products of CEA and homologues thereof, comprising the steps of: (a) identifying gene products expressed by CEA and homologues thereof in a human patient having cancer by isolating a biological sample from the subject, wherein the sample is one that would comprise CEA gene product if the CEA gene were expressed, and (b) utilizing said gene products as biomarkers by contacting the biological sample with the anti-CEA antibody of any one of claim 1-10, or 14-16, or the composition of claim 11 to create a sample-antibody complex, (c) removing any unbound antibody and then contacting the sample-antibody complex with a label specific for the antibody or sample-antibody complex; and (d) detecting the presence of the antigen-antibody complex by detecting the label, wherein detection of the label indicates detection of cancer.

Embodiment 52. A method of determining the status of a cell in a sample comprising:
 a. obtaining said sample from a subject;
 b. contacting said sample with the antibody or antibody fragment of any one of embodiments 1-10, or 14-16, or the composition of claim 11; and
 c. determining the quantity of CEA antigen detected by the antibody or antibody fragment.

Embodiment 53. A method for detecting pancreatic cancer in a patient comprising (a) removing a pancreatic or blood specimen from a patient suspected of or having pancreatic cancer; (b) contacting the specimen with an antibody or antibody fragment of any one of embodiments 1-10, or 14-16, or the composition of claim 11, thereby forming antigen-antibody complexes in said specimen; (c) labeling the specimen with a label specific for the antibody or antigen-antibody complex; (d) detecting the presence of the antigen-antibody complex by detecting the label; and (e) determining the level of CEA antigen as compared to a negative control, wherein a level of CEA antigen that is greater than the negative control is indicative of pancreatic cancer.

Embodiment 54. The method of embodiment 53 wherein the method if performed in vitro.

Embodiment 55. The method of any of embodiments 53-54, wherein the pancreatic cancer is early stage, and the method is capable of detecting CEA antigen at this early stage.

Embodiment 56. The method of any of embodiments 53-55, wherein the pancreatic cancer is in stage I, II, III, or IV, and the method is capable of detecting CEA antigen at this early stage.

Embodiment 57. A kit for the immunohistochemical detection of pancreatic cancer comprising: (a) a monoclonal antibody having heavy chain CDR1, CDR2 and CDR3 sequences comprising SEQ ID NOs: 1, 2 and 3, respectively, and light chain CDR1, CDR2 and CDR3 sequences comprising SEQ ID NOs: 4, 5 and 6, respectively; and (b) a secondary antibody conjugated to a detectable label or a separate non-conjugated detectable label that binds to the secondary antibody, the antibody-antigen complex, or the monoclonal antibody of (a).

Embodiment 58. An immunohistochemical method of detecting pancreatic cancer in a tissue specimen collected from patients comprising the steps of: (a) obtaining a tissue specimen; (b) contacting said tissue specimen with the antibody of antibody fragment of any one of embodiments—10, or 14-16, or the composition of claim 11; (c) after step b), contacting the tissue specimen with a detectable label that binds to the secondary antibody, the antibody-antigen complex, or the antibody; and (d) staining said tissue specimen with an immunohistochemical staining; wherein said staining indicates antibody binding and presence of pancreatic cancer in said tissue specimen.

Embodiment 59. A composition comprising: a tissue specimen; and an antibody-antigen complex between the antibody or antibody fragment of any one of embodiments—10, or 14-16, or the composition of claim 11; wherein said tissue specimen is from a patient suffering from cancer.

Embodiment 60. The composition of embodiment 59, wherein the cancer is colorectal cancer, liver cancer, stomach cancer, ovarian cancer, thyroid cancer, lung cancer, breast cancer, or pancreatic cancer.

Embodiment 61. A use of composition of embodiment 11, or the antibody or antibody fragment of any one of embodiments 1-10 or 11-14, for detecting cancer.

Embodiment 62. The composition of embodiment 61, wherein the cancer is colorectal cancer, liver cancer, stomach cancer, ovarian cancer, thyroid cancer, lung cancer, breast cancer, or pancreatic cancer.

Embodiment 63. A method for monitoring progression of cancer and/or therapeutic efficacy of a cancer therapeutic comprising obtaining an initial sample from a human patient with cancer at a first time point; contacting said sample with an antibody or antibody fragment of any one of embodiments—10, or 14-16, or the composition of claim 11 forming an antigen-antibody complex; labeling the specimen with a label specific for the antigen-antibody complex; and detecting the presence of the antigen-antibody complex by detecting the label; determining the level of CEA antigen detected by the antibody or antibody fragment to determine a baseline level of CEA antigen associated with the patient's cancer; obtaining a second sample at a second (later) timepoint, optionally wherein the second timepoint is after a period of time whereby the subject has been receiving therapy; repeating steps (b) through (e) to determine a second level of CEA antigen associated with the patient's cancer; and determining that the patient's cancer has progressed if the level of CEA antigen at the second timepoint is greater than the level at baseline; and determining that the patient's cancer has regressed if the level of CEA antigen at the second timepoint is less than the level at baseline.

Embodiment 64. The method of embodiment 63, wherein the cancer is colorectal cancer, liver cancer, stomach cancer, ovarian cancer, thyroid cancer, lung cancer, breast cancer, or pancreatic cancer.

Embodiment 65. The method of embodiment 63, wherein the solid tumor cancer is pancreatic cancer.

Embodiment 66. The method of embodiment 63, wherein an increase in the CEA at the second time point is indicative of progression of the cancer.

Embodiment 67. The method of embodiment 63, wherein a decrease in the CEA at the second time point is indicative of regression of the cancer.

Embodiment 68. The method of embodiment 63, wherein the first timepoint is before therapy or at initial diagnosis.

Embodiment 69. The method of embodiment 63, wherein the first timepoint is after therapy or at initial diagnosis.

Embodiment 70. The method of embodiment 63, wherein the second timepoint is after receiving therapy.

Embodiment 71. The method of embodiment 63, wherein the method is performed in vitro.

Embodiment 72. The method of embodiment 69, wherein the therapy is surgery, including a whipple procedure, distal pancreatectomy, and a total pancreatectomy, radiation therapy, proton beam therapy, stereotactic body radiation (SBRT) or cyberknife, immunotherapy, targeted therapy and chemotherapy.

EXAMPLES

Example 1

Antibodies were prepared using native (wt) CEA antigen as immunogen and about 19,200 hybridomas were produced and screened. About 20 promising candidates were further evaluated and five clones were ultimately selected for follow-up as follows. After determination of the IgG isotypes (IgG1, G2, G2a, G2b) of hybridoma clones, the total RNA was extracted from the hybridoma cell line cultures ($2\times10^6$) by the use of RNA Extraction Kit (e.g., Qiagen Mini RNeasy kit) following the kit instruction. The RNA was reverse-transcribed into complementary DNA (cDNA) using Super-Script® III First-Strand Synthesis System (ThermoFisher Scientific, Carlsbad, CA, USA). One (1) µg of cDNA from each sample was subjected to Polymerase Chain Reaction (PCR). The mouse universal Ig Heavy or Light chain primers were used to amplify the V-region of cDNA samples of hybridoma clone (ADx-CEA). Universal primers were designed from the highly conserved regions as described in Dattamajumdar, Anupam K., et al. "Rapid cloning of any rearranged mouse immunoglobulin variable genes." *Immunogenetics* 43.3 (1996): 141-151. The primer pairs H-F and H-R were used to amplify gene H, and the pairs K-F and K-R to amplify gene K. See Table 2. The primer sequences for Heavy-chain were as follows; VH 5'-tgaggtgcagctggaggagtc-3' (SEQ ID NO: 13) and JH 5'-gtgaccgtggtccttggccccag-3'(SEQ ID NO: 14). The primer sequences for Light-chain were as follows; VK 5'-gacattctgatgacccagtct-3' (SEQ ID NO: 15) and JK 5'-ttttatttccagcttggtccc-3'(SEQ ID NO: 16). The pairs are described in Table 2, below. The PCR cycles were conducted at the initial 6 cycle of 94° C. for 15 seconds, 62° C. (−1.2° C./cycle) for 30 seconds and 72° C. for 30 seconds, and then following 30 cycles of 94° C. for 15 seconds, 56° C. for 30 seconds and 72° C. for 30 seconds. One hybridoma was selected as a lead for follow-on testing, and this hybridoma produced antibody ADx-CEA, which has the CDRs of SEQ ID NOs: 1-6, VH of SEQ ID NO:7, VL of SEQ ID NO: 8, full heavy of SEQ ID NO: 9, and full light of SEQ ID NO: 10, as described herein. Throughout, this lead antibody is referred to as ADx-CEA. The amplicon for ADx-CEA are shown in FIG. 1, where the heavy and light chains run at ~380 to 500 bp on 1% agarose.

TABLE 2

| Primer | Primer Sequence | SEQ ID NO. | Gene Amplified | Pair |
|---|---|---|---|---|
| VH | tgaggtgcagctggaggagtc | 13 | H | H-F |
| JH | gtgaccgtggtccttggccccag | 14 | H | H-R |
| VK | gacattctgatgacccagtct | 15 | K | K-F |
| JK- | ttttatttccagcttggtccc | 16 | K | K-R |

Example 2

Figure 2:
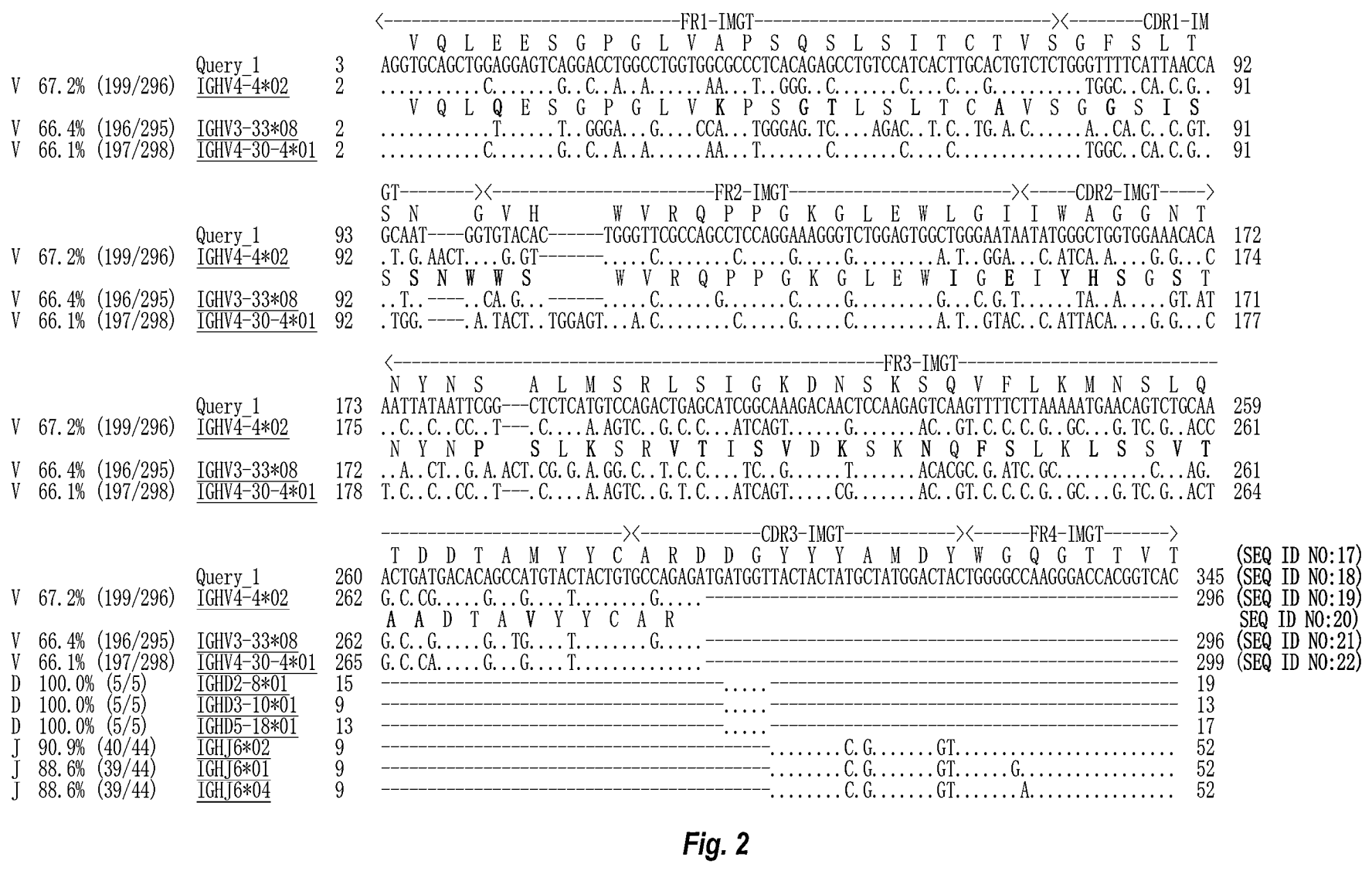

PCR products were purified and amplicons were cloned into pCR4-TOPO vector using the TA cloning strategy (ThermoFisher Scientific, Carlsbad, CA, USA) following manufacturer's instruction. Three (3) to five (5) single colonies were selected, and plasmid DNA was amplified using primers specific for vector DNA sequences. Subcloning was done, where needed. The plasmids from each colony were isolated using Miniprep Kit (Qiagen Inc). The PCR inserts were verified by restriction analysis using EcoR1 digestion and sequenced for both of the chains with the use of M13 universal primers using cycle sequencing reaction with fluorescent dye terminators and capillary-based electrophoresis. DNA sequence data from all the constructs were analyzed and consensus sequences for heavy and light chains were determined. The consensus sequences were compared to all known variable region sequences to rule out artifacts and/or process contamination. Consensus sequences were then analyzed using an online tool to verify that the sequences could encode a productive immunoglobulin. Sequence comparison with the mouse and human databases (GenBank) was performed using BLAST (Basic Local Alignment Search Tool) of NCBI (NIH, Bethesda, MD) against the KABAT database (to identify CDR1 and CDR2) and IMGT/V Quest (to detect CDR3) programs, where the query was ADx-CEA clone's DNA sequence. The representative BLAST results for heavy and light chains of the ADx-CEA is provided in FIGS. 2 and 3. For verification purposes, and as shown in FIGS. 2 and 3, the reference genomic sequences of IGHV4-4*02; IGHV3-33*08 and IGHV4-30-4*01 were found to be the most reliable sequences to detect homology in the V region 66-67%) when blasted against *Homo Sapiens* Ig germline sequences. The most reliable Variable (V) gene match was found to be IGHV4-4*02; the most reliable Diversity (D) gene match was found to be IGHD2-8*01. The most reliable Joining (J) gene segment match was found to be IGHJ6*02.

Example 3

A lead candidate monoclonal antibody was chosen, termed herein as "ADx-CEA". Approximately 1 µg and 5 µg of purified ADx-CEA was suspended in PBS and applied to an SDS-PAGE gel under reducing (boiled 3 minutes in sample buffer with beta-mercaptoethanol and 10% SDS) and non-reducing conditions to 10% Bis-Tris gel (Lanes 3, 5 and 7, 9 respectively). The gel was run at 129 volts, and then stained with Coomassie Blue R350 (0.1% w/v), 20% v/v methanol, and 10% v/v acetic acid, de-stained in 50% v/v methanol in water with 10% v/v acetic acid.

Figure 4:
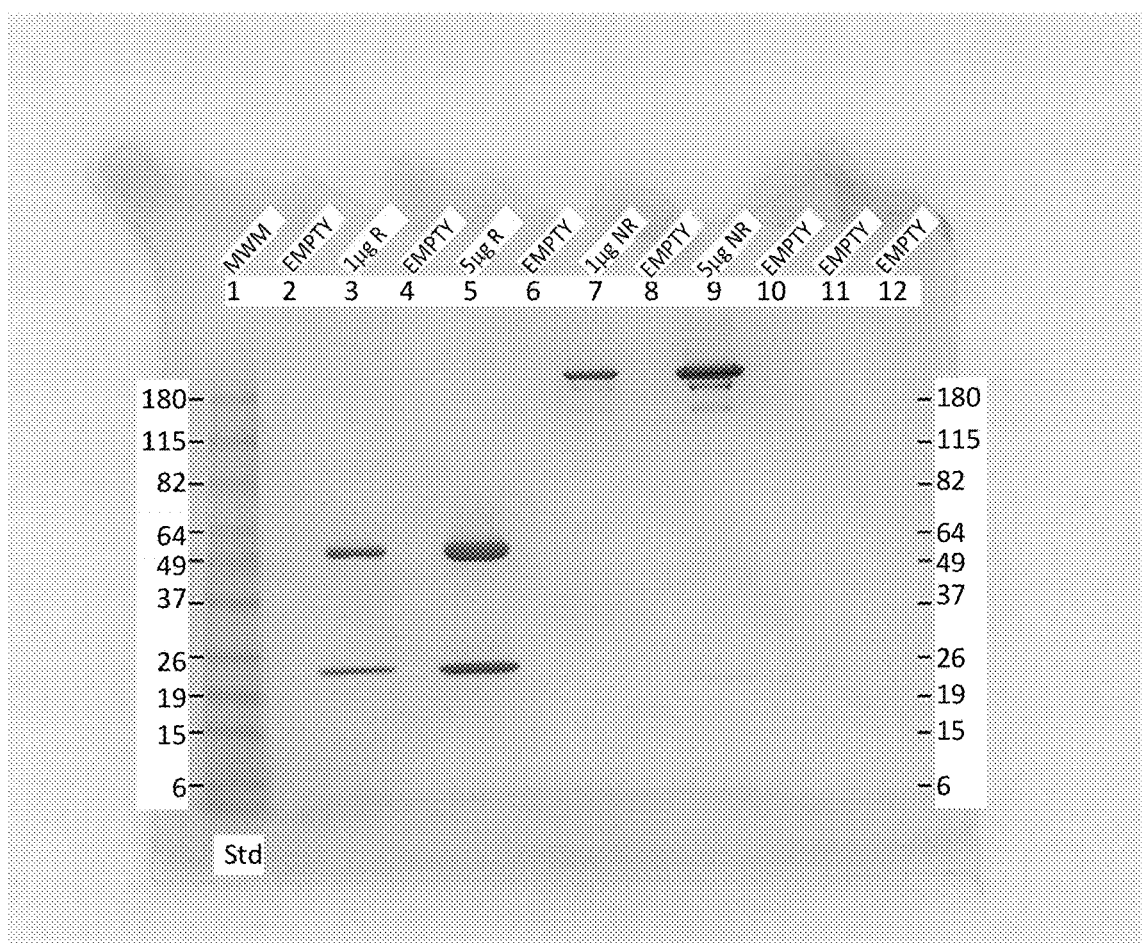
FIG. 4 shows an SDS-PAGE analysis of heavy and light chains of the isolated ADx-CEA.

As depicted in FIG. 4, Lane 3 contained 1 µg of ADx-CEA mAb, reduced. Lane 5 contained 5 µg of ADx-CEA mAb, reduced. Lane 7 contained 1 µg of ADx-CEA mAb, non-reduced. Lane 9 contained 5 µg of ADx-CEA mAb, non-reduced. Under denatured conditions, the heavy chain of ADx-CEA (IgG1 kappa) was detected at ~50 kDa. The light chain of ADx-CEA was detected at ~25 kDa (FIG. 4).

Example 4

A volume of 25 µl of sample buffer containing 50 µs of recombinant CEA (Mybiosource Carcinoembryonic Recombinant Protein, Catalog no. MBS142843) was boiled for 3 minutes and loaded into a 4-12% Tris-Glycine gel, along with 5 µl of molecular markers. The gel was run at 125 V for 1.5 hours. The gel was then transferred to a PVDF membrane. The membrane was incubated with ADx-CEA mAb at 4° C. overnight. After the membrane was rinsed with PBST, it was incubated with secondary antibody (sheep anti-mouse IgG-HRP, 1:1000 diluted in PBST) for one hour, rinsed in PBST. The bands were visualized with 1-Step NBT/BCIP solution.

Figure 5:
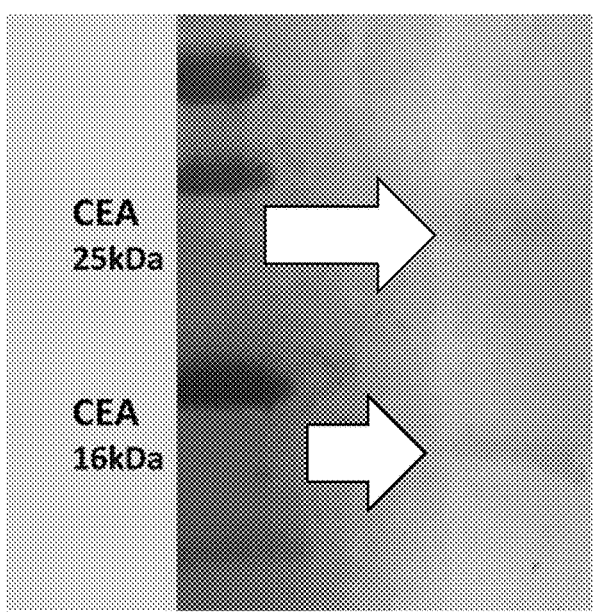
FIG. 5 shows a Western blot analysis of CEA detected by the isolated ADx-CEA.

Under reducing conditions and based on the manufacturer's instructions, ADx-CEA detected two bands at molecular weights for 16 kDa and 25 kDa human CEA protein as shown by the arrows in FIG. 5. FIG. 5 is represented of a repeated experiment.

Example 5

PANC-1 cells (a human pancreatic cancer cell line isolated from a pancreatic carcinoma of ductal cell origin; purchased from ATCC) were cultured on glass-bottomed wells for 18 hours. The cells were fixed with 10% paraformaldehyde and permeabilized with Triton X-100. Cells were washed in PBS and incubated with ADx-CEA (5 µg/ml) for 15 minutes. Cells were washed in PBS and subsequently incubated with FITC-conjugated mouse IgG (4 µg/ml) for 15 minutes. Cells were washed and staining was visualized under an immunofluorescence microscope.

Figure 6B:
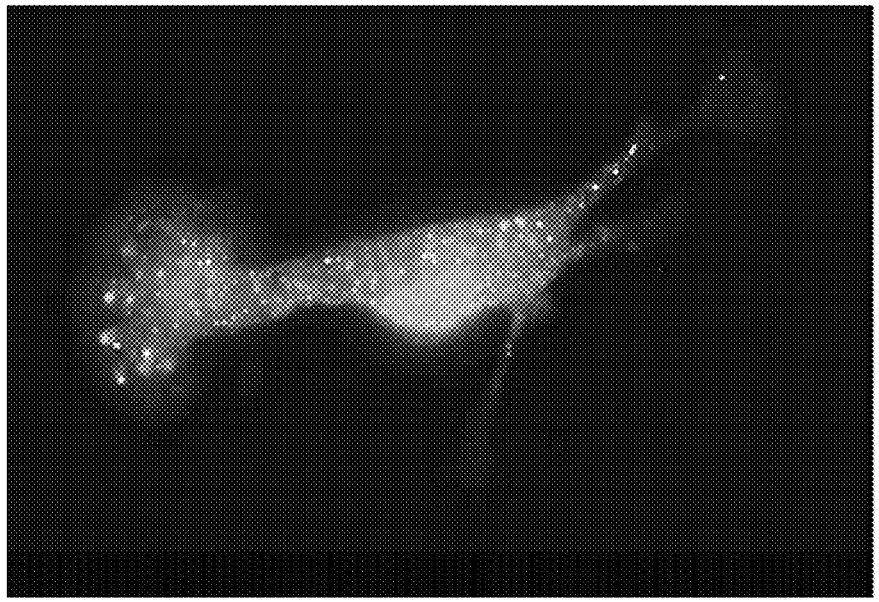
FIGS. 6A-B show the representative image of the indirect immunofluorescence staining of CEA detected by the isolated ADx-CEA that is localized in vesicles in a punctuate manner.
Figure 6A:
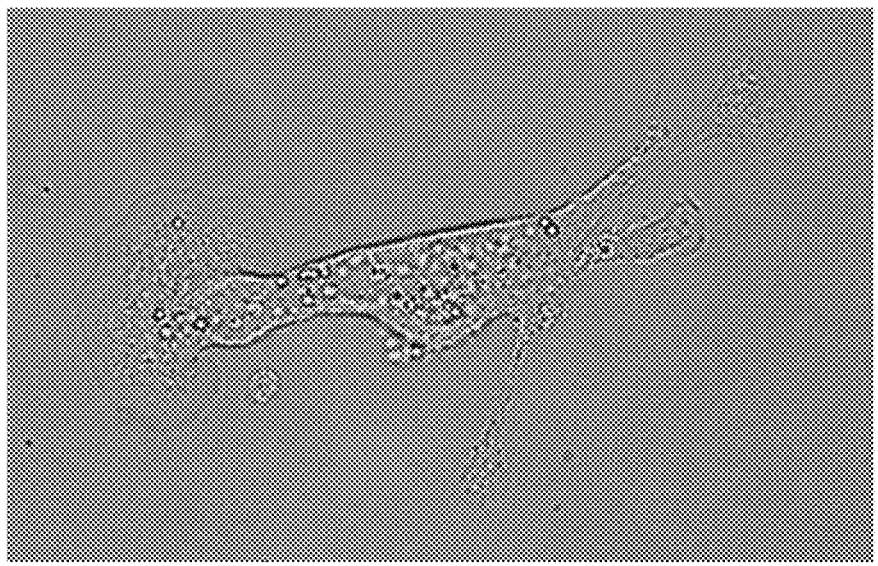

FIGS. 6A-B show representative images of the indirect immunofluorescence staining of CEA detected by ADx-CEA that is localized in vesicles in a punctuate manner. FIG. 6A shows the phase-contrast image. FIG. 6B shows the immunofluorescence staining image.

Example 6

Plasma samples from healthy donors (n=9) and patients (n=17) who were untreated and diagnosed with various stages (IA, IB, IIA, IIB, III, IIIA, IV) of pancreatic cancer were diluted with PBS. Sample buffer was added with the final volume of 25 µl and boiled for 3 minutes. The samples were loaded into a 4-12% Tris-Glycine gel, along with 5 µl of molecular markers. The gel was run at 125 V for 1.5 hours. The gel was then transferred to a PVDF membrane. The membrane was incubated with ADx-CEA at 4° C. overnight. After the membrane was rinsed with PBST, it was incubated with secondary antibody (sheep anti-mouse IgG-HRP, 1:1000 diluted in PBST) for one hour, rinsed in PBST. The bands visualized with 1-Step NBT/BCIP solution.

Figures 7, 8:
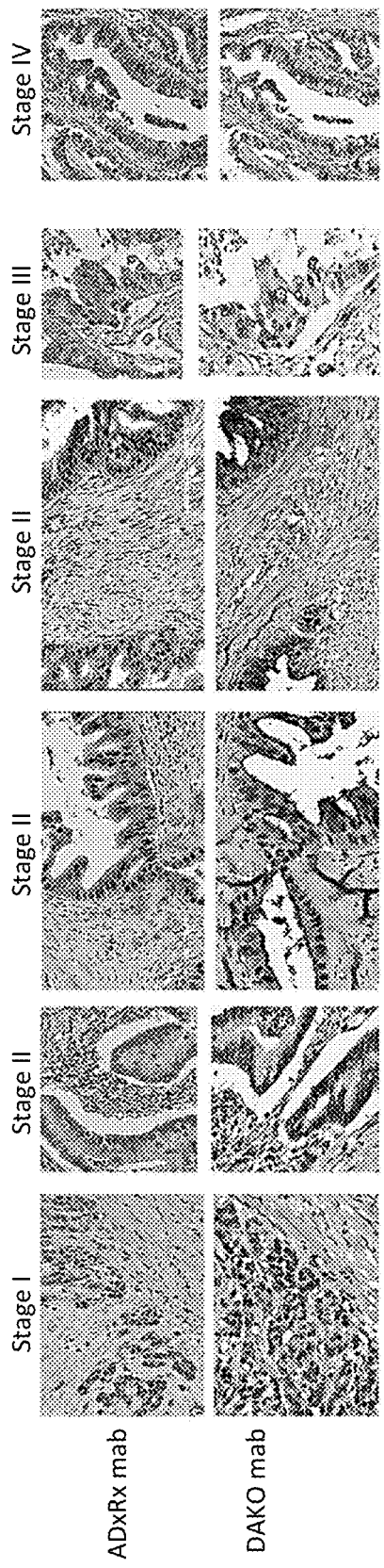
FIG. 7 shows a Western blot analysis of the isolated ADx-CEA in patient samples, wherein the patients have pancreatic cancer, as compared to control.
FIG. 8 depicts IHC staining analysis with ADx-CEA in various stages of pancreatic cancer tissues.

ADx-CEA detected CEA protein in plasma blood samples from healthy donors and patients diagnosed with pancreatic cancer. FIG. 7. CEA protein expression showed variable levels and detected CEA at low levels in healthy blood samples (n=9). Blood analyses of pancreatic cancer patients diagnosed at various stages showed increased levels of CEA protein with stage (n=17).

Example 7

Tissue array slides with formalin fixed paraffin embedded (FFPE) tissue sections were used from BiocoreUSA, Catalog no. BC001157. Slides were deparaffinized in xylene and hydrated through a series of alcohols. Antigen retrieval was performed in a steamer in Citrate-EDTA buffer pH 6.0 for 20 minutes. Slides were treated $H_2O_2$ for 10 minutes, and then treated with the Background Sniper (Biocare Medical, Catalog no. BS966) for 10 minutes. Primary antibody is diluted 1:50 in NDB's Antibody Diluent Buffer for 60 minutes. Detection of the antibody staining was achieved using Biocare Mach 3 reagent with 10-minute incubations for each component. Counterstain was performed using Gill's II Hematoxylin. Then, the slides were dehydrated in alcohol and cleared in xylene and mounted with Permount. Presence of the staining was determined using Lab Vision IHC 360 Autostainer and Dako Link plus IHC System.

ADx-CEA detected pancreatic cancer at early stages. FIG. 8. As shown in FIG. 8, the DAKO anti-human commercially purchased CEA mAb showed false negative staining in various stages of pancreatic cancer tissues that showed partial positive, staining only stage II tissues, but not stage I, III and IV. Meanwhile, ADx-CEA showed positive staining in the same tissues, including stage I-IV tissues. The staining showed membrane, cytoplasmic and pattern and increased expression of the CEA detected as the stage increased. Pathologists confirmed that stained tissues are diagnosed with pancreatic cancer.

Example 8

Immunohistochemical (IHC) staining was performed in a total of 215 tissue samples using ADx-CEA that included healthy normal human tissues (n=19) as well as patient tissues diagnosed with various stages of pancreatic cancer (n=196) using the immunohistochemical (IHC) staining at pathology laboratories (John's Hopkins and CLIA pathology) in total of 215 healthy and pancreatic cancer tissues and compared side by side using commercial FDA approved mouse anti-human CEA antibody from DAKO.

Figure 9A:
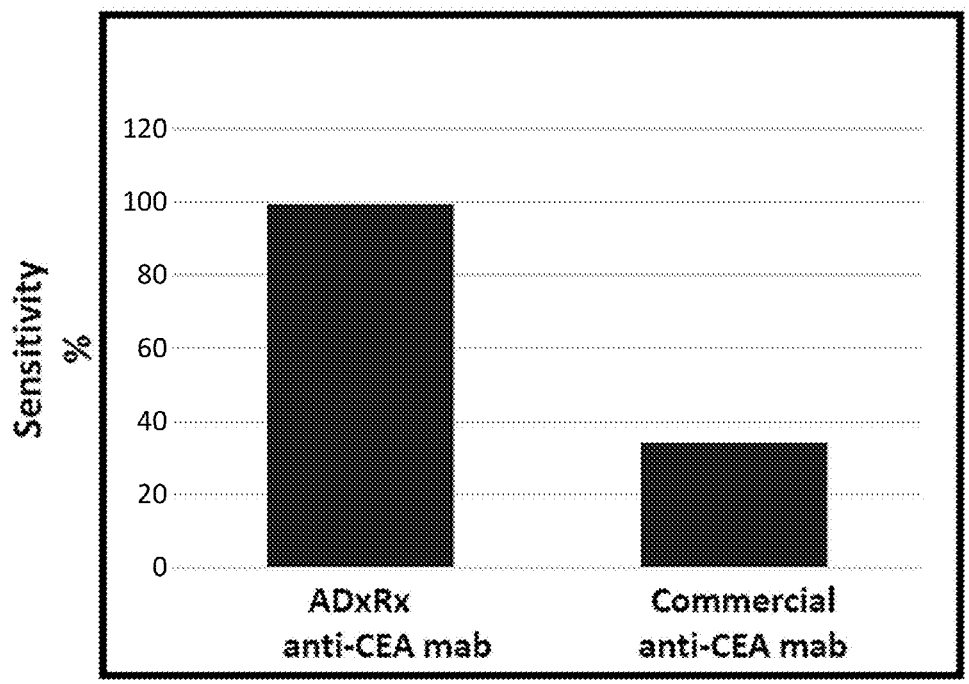
FIGS. 9A-B depict the overall sensitivity and specificity of ADx-CEA.
Figure 9B:
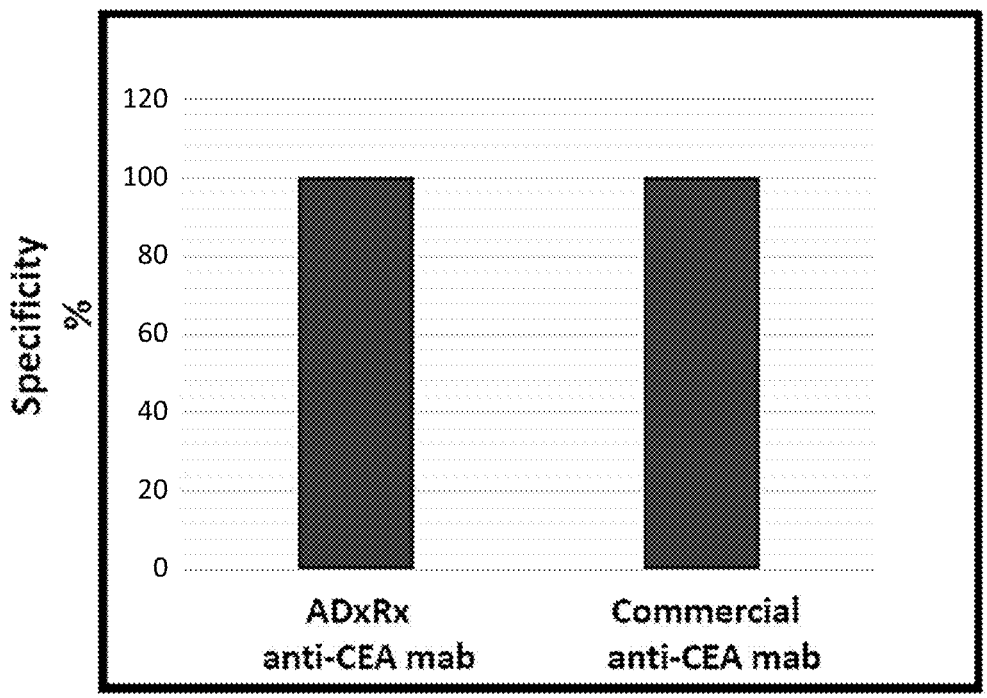
Figure 10A:
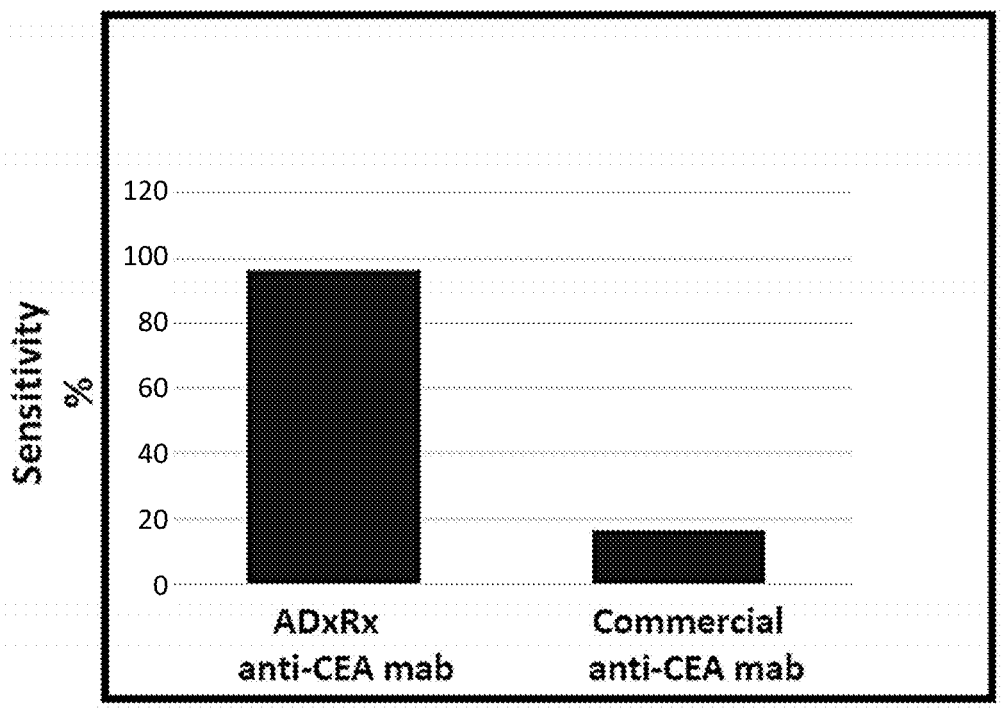
FIGS. 10A-B depict the early stage (I, II) sensitivity and specificity of ADx-CEA.
Figure 10B:
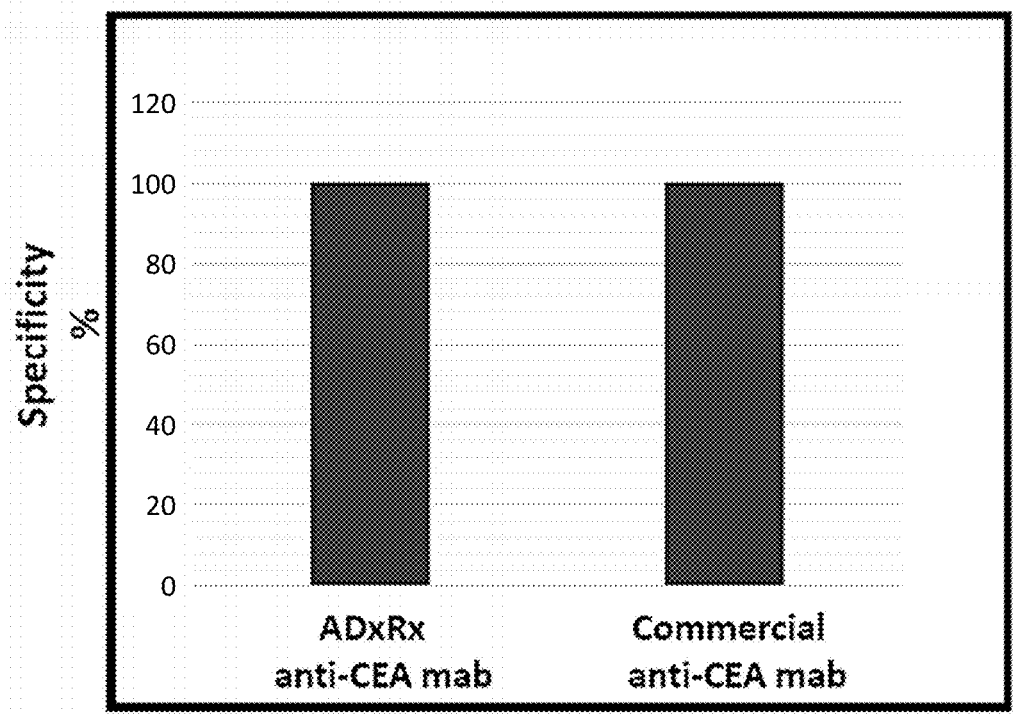
Figure 11A:
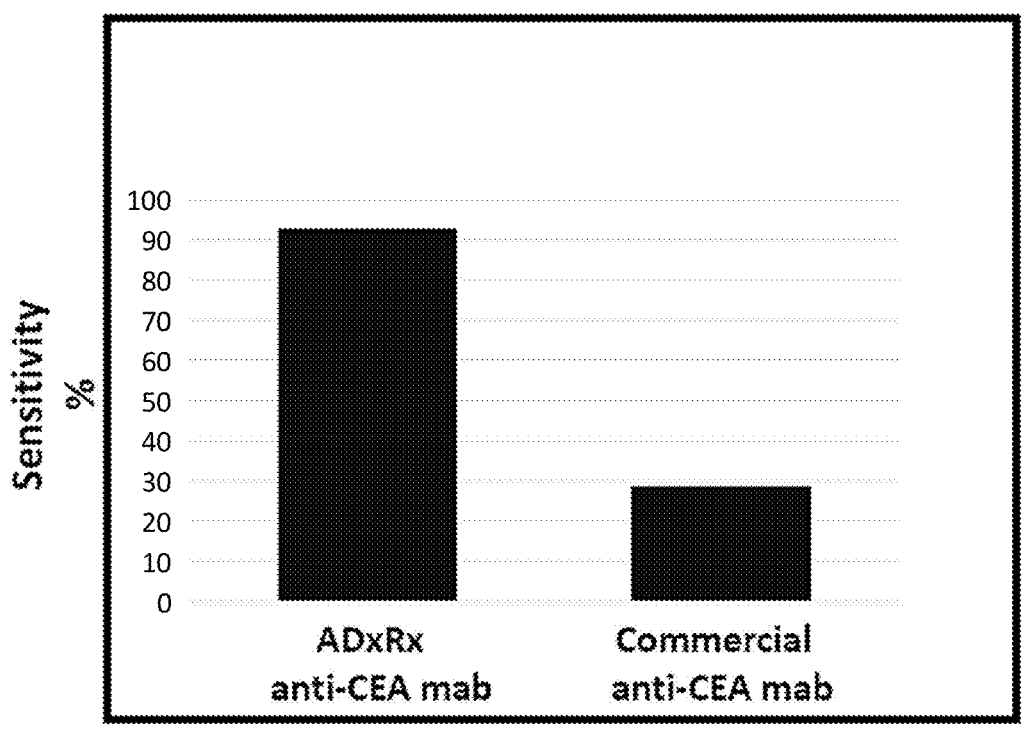
FIGS. 11A-B depict the late-stage (III, IV) sensitivity and specificity of ADx-CEA.
Figure 11B:
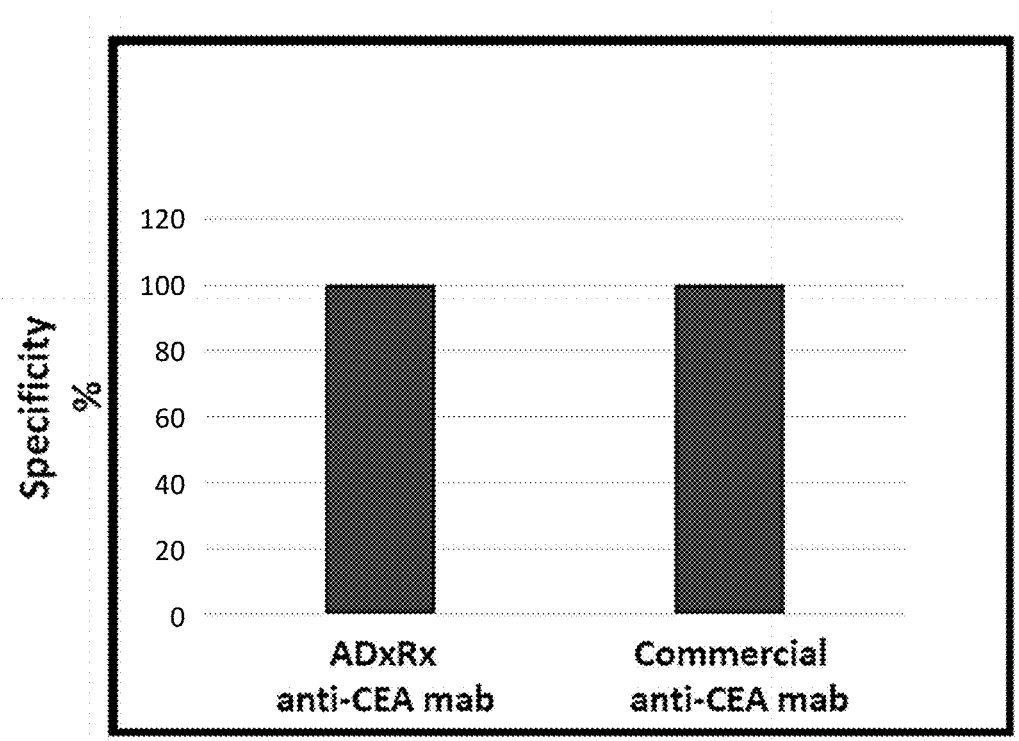

Calculated value of sensitivity of ADx-CEA was 99.5% while commercial mAb was 34% as shown in Tables 3-5 and FIGS. 9A-B. Early stage (I, II) sensitivities and specificities are shown in FIGS. 10A-B. Late stage (III, IV) sensitivities and specificities are shown in FIGS. 11A-B.

TABLE 3

(Summary):

|  | ADx-CEA | Commercial FDA approved mAb |
|---|---|---|
| Sensitivity (%) | 99.5 | 34 |
| Specificity (%) | 100 | 100 |

Tables 4-5 display frequency distribution and corresponding sensitivity and specificity.

TABLE 4

ADx-CEA

|  | Disease Pancreatic Cancer | No Disease No Pancreatic Cancer | Total |
|---|---|---|---|
| Positive | 195 | 0 | 195 |
| Negative | 1 | 19 | 20 |
| Total | 196 | 19 | 215 |

Sensitivity of ADx-CEA (ESTIMATED using data in Table 4): 195/196=0.9948×100=99.5%

Specificity of ADx-CEA (ESTIMATED using data in Table 4): 19/19=1.00×100=100%

TABLE 5

Commercial anti-CEA Antibody

|  | Disease Pancreatic Cancer | No Disease No Pancreatic Cancer | Total |
|---|---|---|---|
| Positive | 66 | 0 | 66 |
| Negative | 130 | 19 | 149 |
| Total | 196 | 19 | 215 |

Sensitivity of DAKO-CEA (ESTIMATED using data in Table 5): 66/196=0.3367×100=34%

Specificity of DAKO-CEA (ESTIMATED using data in Table 5): 19/19=1.00×100=100%

Example 9

The human BxPC-3 pancreatic adenocarcinoma cell line was purchased from American Type Culture Collection (Manassas, VA, USA). Cells were cultured in RPMI-1640; American Type Culture Collection, Manassas, VA, USA) supplemented with 10% fetal bovine serum (FBS; Thermostat Scientific, Inc.), and maintained at 37° C. in a 5% CO2 atmosphere.

Soft agar colony formation assay: BxPC-3 cells (2,000 cells) were suspended with ADx-CEA or only in PBS in 0.3% Noble agar (Difco; BD Biosciences, Franklin Lakes, NJ, USA) in RPMI-1640 supplemented with 10% FBS and overlaid on 0.8% Noble agar in 12-well tissue culture plates. Colonies were allowed to grow for 2.5 weeks in the growth medium, colony formation was observed and counted for data analysis.

Figure 12A:
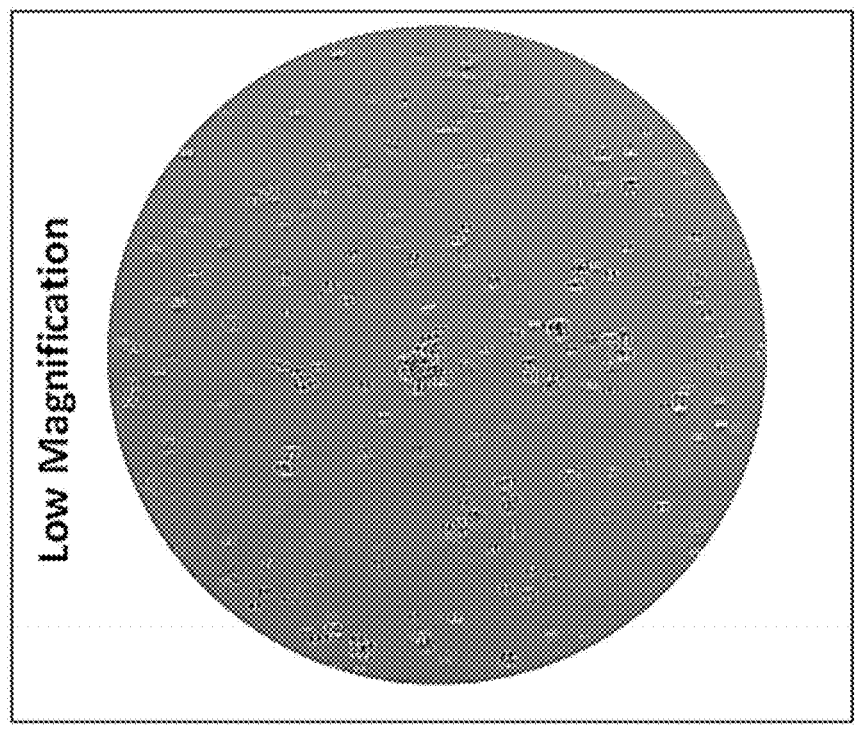
FIGS. 12A-C depicts soft agar coronary formation and related data.
Figure 12B:
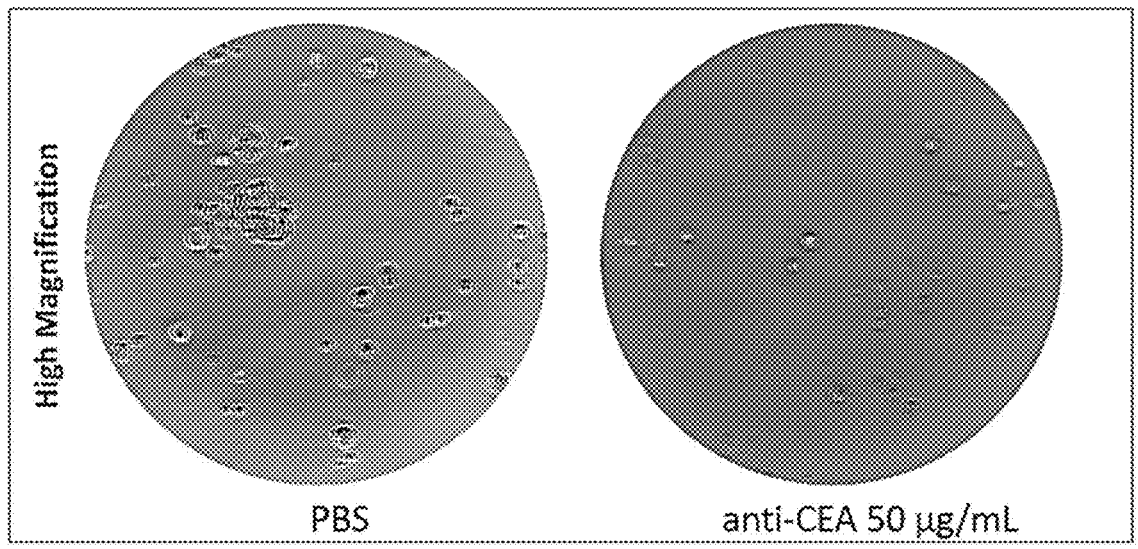

BxPC-3 cells were cultured in soft agar in the absence (PBS only) and presence of different concentration of ADx-CEA. After 2.5 weeks, colonies were imaged using an inverted microscope (FIGS. 12A-B). Picture of wells are representative of three independent experiments.

Figure 12C:
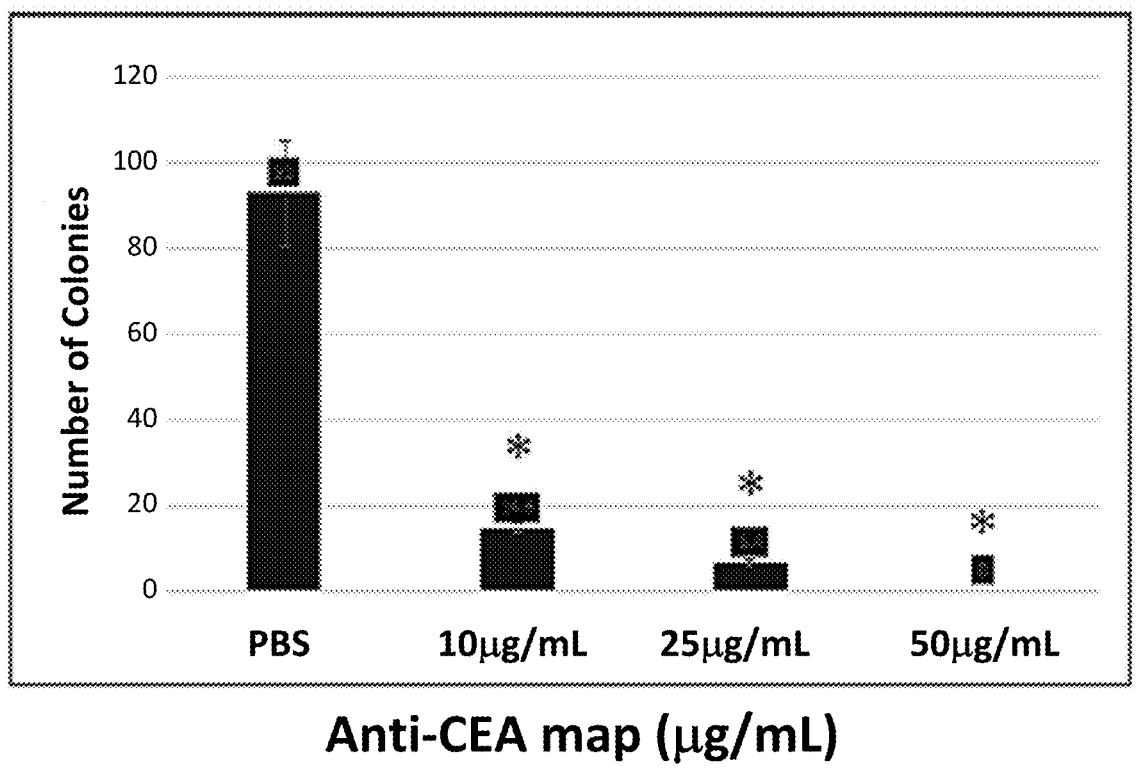

BxPC-3 cells were grown in soft agar in PBS, or 10, 25 and 50 μg/mL ADx-CEA. After 2.5 weeks, individual colonies larger than 70 μm were counted. Experiments were repeated three times. The statistical significance of total colony count difference between the control and treated samples was determined by Student's t-test (*p <0.005) (FIG. 12C). BxPC-3 cells showed a marked decrease in a dose-dependent manner in colony formation in the presence of 10 μg/mL, 25 μg/mL and 50 μg/mL ADx-CEA.

Example 10

Figure 13A:
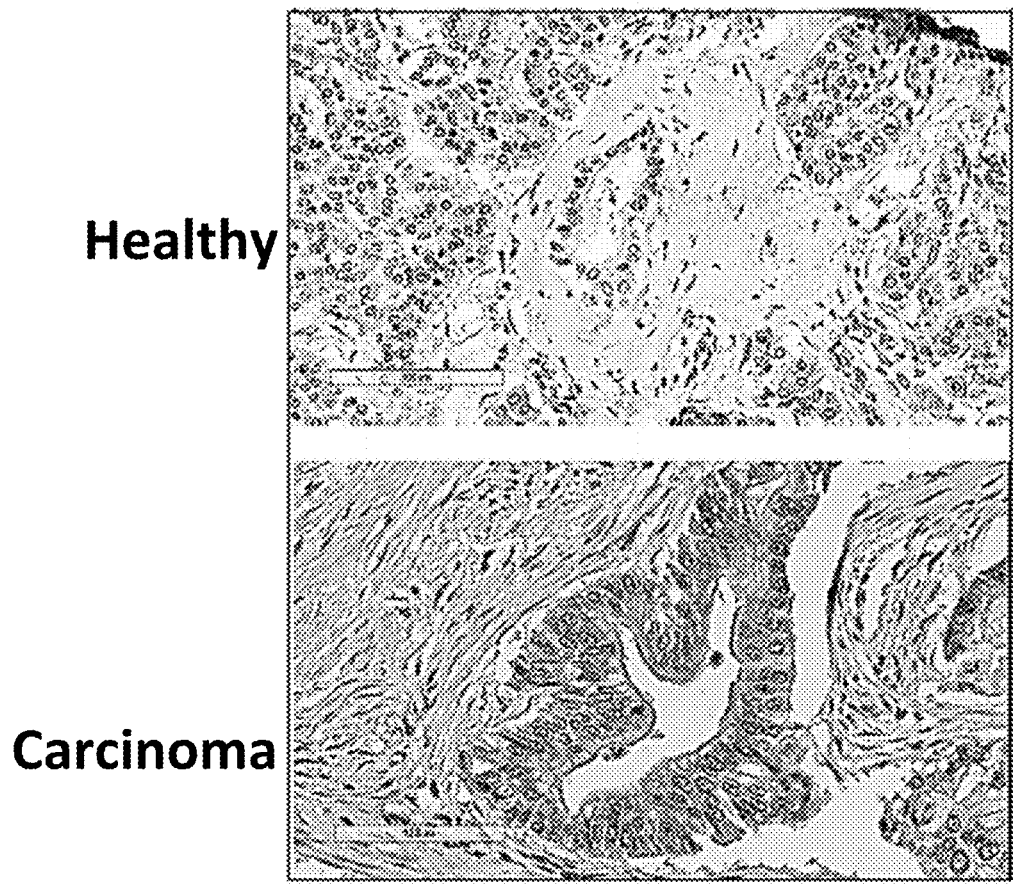
FIGS. 13A-C depicts CEA expression in various formalin fixed paraffin embedded (FFPE) human tissues via IHC staining. CEA protein expression was validated in healthy and cancerous tissues from healthy individuals and cancer patients using ADx-CEA. Pancreatic, colon and the liver carcinoma tissues showed positive membraneous and cytoplasmic staining for CEA expression.
Figure 13B:
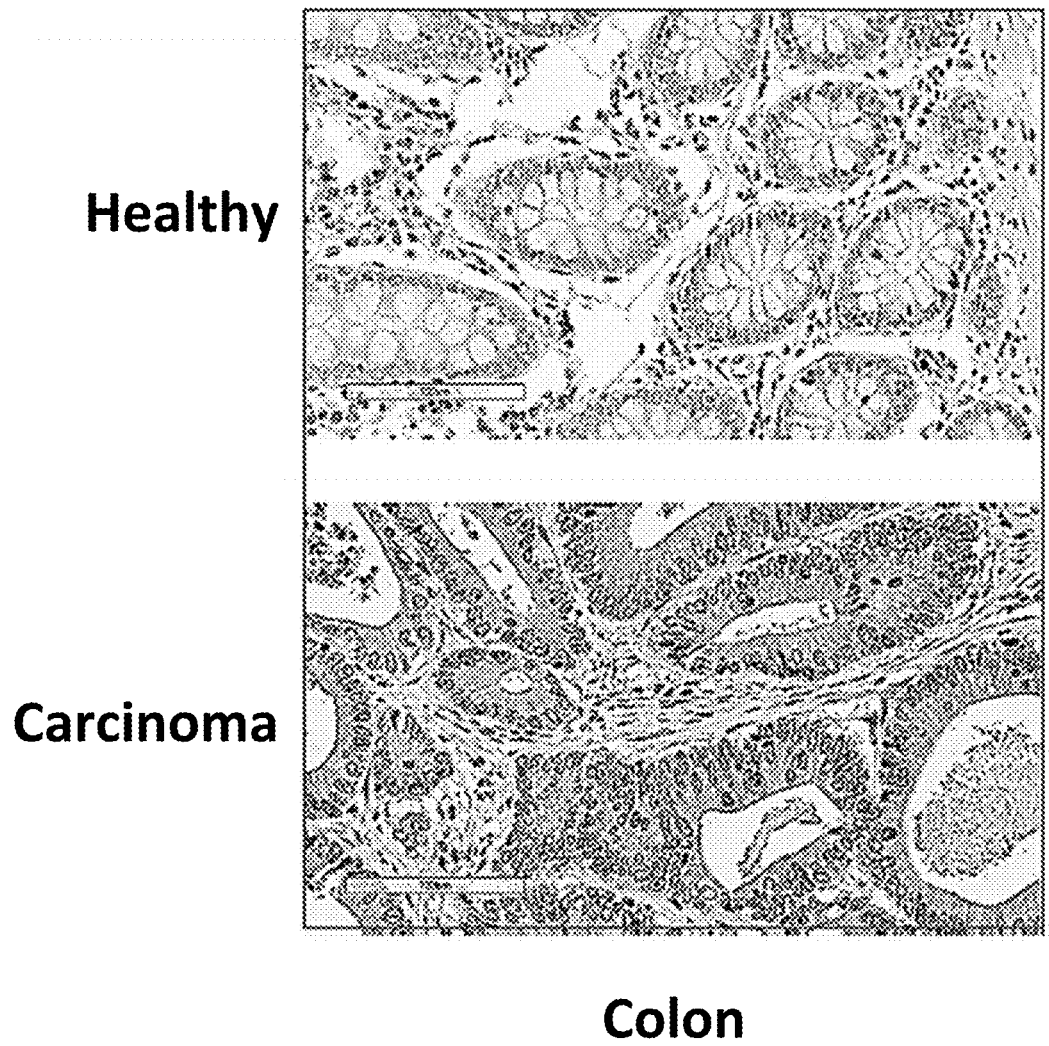
Figure 13C:
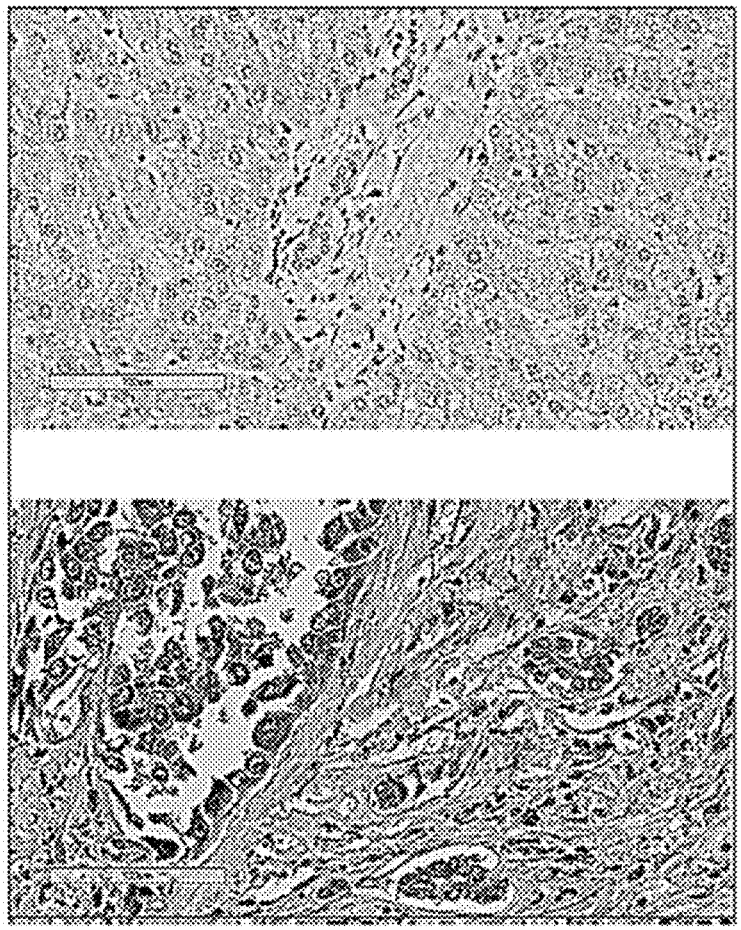

CEA protein expression was validated in healthy and cancerous tissues from healthy individuals and cancer patients using the ADx-CEA described herein using IHC staining. The antibody was tested against tissue from the following: breast, lymph, cervix, prostate, pancreas, ovary, bladder, kidney, uterus, colon, liver, brain, rectum, esophagus, stomach, lung and uterus. The pancreatic (FIG. 13A), colon (FIG. 13B) and the liver (FIG. 13C) carcinoma tissues showed positive membraneous, cytoplasmic staining for CEA expression. The breast and kidney carcinoma showed weak staining (data not shown). Tissues from the lymph, cervix, prostate, ovary, esophagus, bladder, uterus, brain, stomach, uterus, lung and rectum showed negative staining for CEA expression (data not shown).

What is claimed is:

1. An isolated antibody or antibody fragment comprising, an (a) HCDR1 comprising the amino acid sequence of SEQ ID NO: 1; (b) HCDR2 comprising the amino acid sequence of SEQ ID NO: 2; (c) HCDR3 comprising the amino acid sequence of SEQ ID NO: 3; (d) LCDR1 comprising the amino acid sequence of SEQ ID NO: 4; (e) LCDR2 comprising the amino acid sequence of SEQ ID NO: 5; and (f) LCDR3 comprising the amino acid sequence of SEQ ID NO: 6.

2. The isolated antibody or antibody fragment of claim 1, wherein the antibody comprises a heavy chain variable region ($V_H$) and a light chain variable region ($V_L$), wherein the $V_H$ comprises the amino acid sequence of SEQ ID NO: 7 and SEQ ID NO: 3 and the $V_L$ comprises the amino acid sequence of SEQ ID NO: 8 and SEQ ID NO: 6.

3. The isolated antibody or antibody fragment of claim 1, wherein the antibody is a monoclonal antibody, a fully human antibody, or an antibody fragment selected from a Fab, Fab', Fv, scFv and (Fab')$_2$.

4. A composition comprising the antibody or antibody fragment of claim 1 and a pharmaceutically acceptable carrier.

5. A kit for the immunohistochemical detection of a solid tumor cancer comprising cells expressing a CEA antigen comprising: (a) an antibody according to claim 1; and (b) a secondary antibody conjugated to a detectable label, wherein the secondary antibody binds to and is capable of detecting the antibody of (a) when bound to a CEA antigen.

* * * * *